(12) United States Patent
Turner et al.

(10) Patent No.: US 8,231,595 B2
(45) Date of Patent: Jul. 31, 2012

(54) STRETCHABLE LAMINATES OF NONWOVEN WEB(S) AND ELASTIC FILM

(75) Inventors: Robert Haines Turner, Cincinnati, OH (US); Donald Zgoda, West Chester, OH (US); Walter Douglas Daniels, Maineville, OH (US); Jim Thomas Bader, Hamilton, OH (US); Erika Fabiola Galvis, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 197 days.

(21) Appl. No.: 12/756,226

(22) Filed: Apr. 8, 2010

(65) Prior Publication Data

US 2010/0262105 A1    Oct. 14, 2010

Related U.S. Application Data

(60) Provisional application No. 61/167,628, filed on Apr. 8, 2009.

(51) Int. Cl.
*A61F 13/15* (2006.01)
*D04H 1/00* (2006.01)

(52) U.S. Cl. .......... 604/385.22; 604/367; 604/366; 604/365; 604/361; 604/368; 156/160; 156/161; 442/361; 442/328; 442/327

(58) Field of Classification Search ........... 604/385.22, 604/385.24, 385.25, 385.26, 385.27, 366, 604/361, 365, 367, 368; 156/160–167; 442/361, 442/328, 327
See application file for complete search history.

(56) References Cited

U.S. PATENT DOCUMENTS

| | | | |
|---|---|---|---|
| 3,338,992 | A | 8/1967 | Kinney et al. |
| 3,692,613 | A | 9/1972 | Pederson |
| 3,802,817 | A | 4/1974 | Matsuki et al. |
| 4,405,297 | A | 9/1983 | Appel et al. |
| 5,167,897 | A | 12/1992 | Weber et al. |
| 5,540,976 | A | 7/1996 | Shawver et al. |
| 5,665,300 | A | 9/1997 | Brignola et al. |
| 5,789,065 | A | 8/1998 | Haffner et al. |
| 5,804,286 | A | 9/1998 | Quantrille et al. |
| 5,940,887 | A | 8/1999 | Rajala et al. |
| 6,001,460 | A | 12/1999 | Morman et al. |
| 6,069,097 | A | 5/2000 | Suzuki et al. |

(Continued)

FOREIGN PATENT DOCUMENTS

CN    101824182    9/2010

(Continued)

OTHER PUBLICATIONS

International Search Report.

*Primary Examiner* — Jacqueline F. Stephens
(74) *Attorney, Agent, or Firm* — Thibault Fayette

(57) ABSTRACT

A stretchable laminate, a process of making a stretchable laminate and a disposable absorbent article that includes a stretchable laminate are disclosed. The stretchable laminate includes a nonwoven web and a web of elastomeric material. The nonwoven web includes two layers of spunbond multi-component fibers and one layer of meltblown fibers. The multi-component fibers include a first polymer and a second polymer having different melt temperatures. Thermo-bonds are formed at least partially through the nonwoven web. Some of the thermo-bonds can be elongated in the cross-machine direction of the nonwoven web.

20 Claims, 15 Drawing Sheets

U.S. PATENT DOCUMENTS

| | | | |
|---|---|---|---|
| 6,124,001 | A | 9/2000 | Sugita et al. |
| 6,169,151 | B1 | 1/2001 | Waymouth et al. |
| 6,506,698 | B1 * | 1/2003 | Quantrille et al. ............ 442/361 |
| 6,518,378 | B2 | 2/2003 | Waymouth et al. |
| 6,531,025 | B1 | 3/2003 | Lender et al. |
| 6,555,643 | B1 | 4/2003 | Rieger |
| 6,559,262 | B1 | 5/2003 | Waymouth et al. |
| 6,978,486 | B2 | 12/2005 | Zhou et al. |
| 7,316,840 | B2 | 1/2008 | Neculescu et al. |
| 7,329,621 | B2 | 2/2008 | Collier, IV et al. |
| 7,335,273 | B2 | 2/2008 | Neculescu et al. |
| 7,422,991 | B2 | 9/2008 | Baldauf et al. |
| 7,438,777 | B2 | 10/2008 | Pourdeyhimi et al. |
| 7,470,340 | B2 | 12/2008 | Baldauf et al. |
| 7,491,666 | B2 | 2/2009 | Smith et al. |
| 7,510,758 | B2 | 3/2009 | Thomas et al. |
| 7,582,178 | B2 | 9/2009 | Hughes et al. |
| 7,585,382 | B2 | 9/2009 | Hughes et al. |
| 7,612,001 | B2 | 11/2009 | Thomas et al. |
| 7,662,745 | B2 | 2/2010 | Zhang et al. |
| 7,674,733 | B2 | 3/2010 | Wu et al. |
| 7,687,415 | B2 | 3/2010 | Tsai et al. |
| 7,692,278 | B2 | 4/2010 | Periaman et al. |
| 7,704,901 | B2 | 4/2010 | Baldauf et al. |
| 7,713,894 | B2 | 5/2010 | Tsai et al. |
| 7,732,948 | B2 | 6/2010 | Caggiano |
| 7,794,819 | B2 | 9/2010 | Black et al. |
| 7,811,949 | B2 | 10/2010 | Snowden et al. |
| 7,855,316 | B2 | 12/2010 | Meyer et al. |
| 7,910,795 | B2 | 3/2011 | Thomas et al. |
| 7,922,854 | B2 | 4/2011 | Sabbagh et al. |
| 7,938,921 | B2 | 5/2011 | Ng et al. |
| 2002/0055316 | A1 | 5/2002 | Araida et al. |
| 2003/0125696 | A1 | 7/2003 | Morman et al. |
| 2004/0087235 | A1 | 5/2004 | Morman et al. |
| 2004/0121683 | A1 | 6/2004 | Jordan et al. |
| 2004/0121692 | A1 | 6/2004 | Taylor et al. |
| 2005/0287892 | A1 | 12/2005 | Fouse et al. |
| 2006/0143767 | A1 | 7/2006 | Yang et al. |
| 2006/0225835 | A1 | 10/2006 | Schonbeck |
| 2006/0246804 | A1 | 11/2006 | Thomas et al. |
| 2006/0251858 | A1 | 11/2006 | Thomas et al. |
| 2007/0088116 | A1 | 4/2007 | Abba et al. |
| 2007/0117934 | A1 | 5/2007 | He et al. |
| 2007/0141311 | A1 | 6/2007 | Mleziva et al. |
| 2007/0141930 | A1 | 6/2007 | Thomas et al. |
| 2008/0003911 | A1 | 1/2008 | Sabbagh et al. |
| 2008/0119102 | A1 | 5/2008 | Hughes et al. |
| 2008/0124563 | A1 | 5/2008 | Shima |
| 2009/0068422 | A1 | 3/2009 | Pascavage |
| 2009/0159187 | A1 | 6/2009 | Ashraf |
| 2009/0258210 | A1 | 10/2009 | Iyad et al. |
| 2009/0264844 | A1 | 10/2009 | Autran et al. |
| 2009/0286893 | A1 | 11/2009 | Shih |
| 2009/0325447 | A1 | 12/2009 | Austin et al. |
| 2009/0325448 | A1 | 12/2009 | Welch et al. |
| 2010/0040826 | A1 | 2/2010 | Autran et al. |
| 2010/0076390 | A1 | 3/2010 | Norrby et al. |
| 2010/0168704 | A1 | 7/2010 | Thomas et al. |
| 2010/0191206 | A1 | 7/2010 | Hird et al. |
| 2010/0215923 | A1 | 8/2010 | Frost |
| 2010/0262110 | A1 | 10/2010 | Lakso |
| 2010/0264376 | A1 | 10/2010 | Korzhenko et al. |
| 2011/0066126 | A1 | 3/2011 | Mansfield |
| 2012/0083178 | A1 | 4/2012 | Sabbagh et al. |

FOREIGN PATENT DOCUMENTS

| | | |
|---|---|---|
| CN | 101921451 A | 12/2010 |
| CN | 101462394 B | 11/2011 |
| CN | 101864102 B | 11/2011 |
| EP | 1 256 594 A1 | 11/2002 |
| WO | WO-01-47710 A1 | 7/2001 |
| WO | WO-2008-070064 A2 | 6/2008 |
| WO | WO-2009-073474 A2 | 6/2009 |
| WO | WO-2009-091796 A2 | 7/2009 |
| WO | WO-2010-102742 A1 | 9/2010 |

* cited by examiner

STRETCHABLE LAMINATES OF NONWOVEN WEB(S) AND ELASTIC FILM

CROSS REFERENCE TO RELATED APPLICATION

This application claims the benefit of U.S. Provisional Application No. 61/167,628, filed Apr. 8, 2009, the substance of which is incorporated herein by reference.

FIELD OF THE INVENTION

The disclosure generally relates to stretchable laminates of nonwoven web(s) and a film that may be an elastic film. The disclosure also relates to processes of making such stretchable laminates and articles incorporating such stretchable laminates.

BACKGROUND OF THE INVENTION

Stretchable laminates that include at least a nonwoven fibrous web bonded to an elastic film are well known in the art. These laminates are particularly useful when used to make at least one of the numerous elements that ultimately form disposable absorbent articles such as diapers, pants and adult incontinence products. For example, stretchable laminates may be used to make stretchable elements such as stretchable ears, stretchable side panels or a stretchable outer cover for an absorbent article. Among other benefits, these stretchable elements provide a better fit of the absorbent article on the user. A typical stretchable laminate that includes a fibrous nonwoven web bonded to an elastic film may be relatively hard to elongate by a caregiver or a user unless the laminate as been mechanically "activated." During mechanical activation, the stretchable laminate is strained to allow the laminate to at least partially recover some of the ease of elongation that the elastic film had before its bonding to the nonwoven web. Some nonwoven webs, such as webs made of carded staple fibers, are easily stretchable or elongatable even when bonded to an elastic film. During mechanical activation, carded webs offer relatively little resistance and, as a result, a stretchable laminate that includes such carded webs can be pre-strained to a great extent without causing either the carded web or the elastic film to tear completely. The main drawback of carded webs is their cost in comparison to other nonwoven webs such as webs that include a layer of spunbond fibers. The relatively inexpensive manufacturing process used to make spunbond type nonwoven webs can make them particularly attractive for use in a stretchable laminate but these webs tend to be much more difficult to elongate without causing the spunbond web and/or the elastic film to tear during the mechanical activation of the laminate. Due to their manufacturing process, spunbond webs may also have local variations in their basis weight that can cause the spunbond web and the elastic film to tear during mechanical activation. A stretchable laminate whose elastic film is torn cannot be used and must be discarded causing undesirable waste and expenses. A stretchable laminate whose nonwoven web is repeatedly torn may be unpleasant to the touch when the laminate is elongated by a caregiver or a user. A nonwoven web that is partially or completely torn offers little or no resistance to limit the elongation of the overall stretchable laminate which in turn may potentially lead to the failure of the stretchable element made of the laminate if a caregiver or user elongates the elements abusively.

It is therefore an object of the invention to provide a stretchable laminate that includes a spunbond nonwoven web bonded to an elastic film to form a laminate that is able to endure mechanical activation without causing the spunbond nonwoven web or the elastic film to tear. It is also an object of the invention to provide a process for making such a stretchable laminate. It is still an object of the invention to provide an article having at least one element that includes such a stretchable laminate.

It is believed that at least some of the objects of the invention can be accomplished by stretchable laminates that include a nonwoven web having a spunbond layer made of bi-component fibers of a certain type. It is also believed that at least some of the objects of the invention can be accomplished by stretchable laminates that include a nonwoven web having a spunbond layer having a more uniform basis weight.

SUMMARY OF THE INVENTION

In one embodiment, the invention is directed to a stretchable laminate that comprises:
 a. a first nonwoven web, said first nonwoven web comprising:
  a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and a cross-machine direction;
  a second layer of fibers comprising meltblown fibers, said second layer having a top and a bottom surface wherein said the top surface of said second layer faces said bottom surface of said first layer; and
  a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;
 wherein said first nonwoven web comprises a plurality of thermo-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction;
 and
 b. a web of an elastomeric material having top and bottom surfaces,
 wherein the bottom surface of said third layer comprising spunbond fibers of said first nonwoven web is bonded to said top surface of said elastomeric web to form a laminate.

In another embodiment, the invention is directed to a process of making a stretchable laminate that comprises:
 obtaining a first nonwoven web, said first nonwoven web comprising:

a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and za cross-machine direction;

a second layer of fibers comprising meltblown fibers, said second layer having a top and a bottom surface wherein said the top surface of said second layer faces said bottom surface of said first layer; and a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;

wherein said first nonwoven web comprises a plurality of thermo-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction;

obtaining a web of an elastomeric material having top and bottom surfaces; and bonding the bottom surface of one of said third layer comprising spunbond fibers of said first nonwoven web to said top surface of said elastomeric web.

In another embodiment, the invention is directed to a disposable absorbent article that comprises:

a chassis having opposing first and second longitudinal side edges, said chassis comprising a liquid pervious topsheet, a liquid impervious backsheet and an absorbent core disposed between said topsheet and said backsheet; and a pair of stretchable ears or side panels connected to each longitudinal side edge of said chassis, each of said ears or side panels comprising a stretchable laminate comprising:

a. a first nonwoven web, said first nonwoven web comprising:

a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and a cross-machine direction;

a second layer of fibers comprising meltblown fibers, said second layer having a top and a bottom surface wherein said the top surface of said second layer faces said bottom surface of said first layer; and a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;

wherein said first nonwoven web comprises a plurality of thermo-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction;

and;

b. a web of an elastomeric material having top and bottom surfaces, wherein the bottom surface of said third layer comprising spunbond fibers of said first nonwoven web is bonded to said top surface of said elastomeric web to form a laminate.

DETAILED DESCRIPTION OF THE INVENTION

Figure 1:
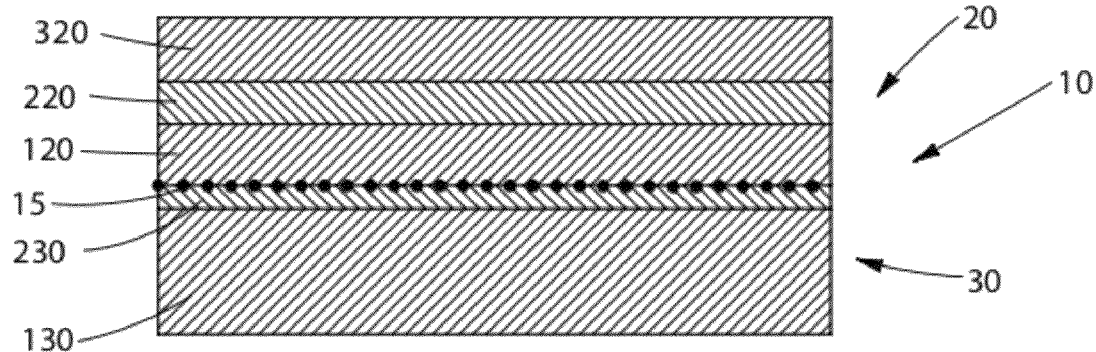
FIG. 1 is a schematic cross-sectional view of a stretchable laminate in accordance with an embodiment of the invention.

As used herein, the term "activated" refers to a material which has been mechanically deformed in order to increase the extensibility of at least a portion of the material. A material may be activated by, for example, incrementally stretching the material in at least one direction.

As used herein, the terms "carded staple fibers" refer to fibers that are of a discrete length which are sorted, separated, and at least partially aligned by a carding process. For example, a carded web refers to a web that is made from fibers which are sent through a combing or carding unit, which separates or breaks apart and aligns the fibers in, e.g., the machine direction to form a generally machine direction-oriented fibrous non-woven web. Carded staple fibers may or may not be bonded after being carded.

As used herein, the terms "elongatable material" "extensible material" or "stretchable material" are used interchangeably and refer to a material that, upon application of a biasing force, can stretch to an elongated length of at least 150% of its relaxed, original length (i.e. can stretch to 50% more than its original length), without complete rupture or breakage as measured by Tensile Test described in greater detail below. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric. For example, an elastic material that has an initial length of 100 mm can extend at least to 150 mm, and upon removal of the force retracts to a length of at least 145 mm (i.e., exhibiting a 10% recovery).

As used herein, the term "film" refers generally to a relatively nonporous material made by a process that includes extrusion of, e.g., a polymeric material through a relatively narrow slot of a die. The film may be impervious to a liquid and pervious to an air vapor, but need not necessarily be so. Suitable examples of film materials are described in more detail hereinbelow.

As used herein, the term "layer" refers to a sub-component or element of a web. A "layer" may be in the form of a plurality of fibers made from a single beam on a multibeam nonwoven machine (for example a spunbond/meltblown/spunbond nonwoven web includes at least one layer of spunbond fibers, at least one layer of meltblown fibers and at least one layer of spunbond fibers) or in the form of a film extruded or blown from a single die.

As used herein, the term "machine direction" or "MD" is the direction that is substantially parallel to the direction of travel of a web as it is made. Directions within 45 degrees of the MD are considered to be machine directional. The "cross direction" or "CD" is the direction substantially perpendicular to the MD and in the plane generally defined by the web. Directions within 45 degrees of the CD are considered to be cross directional.

As used herein, the term "meltblown fibers" refers to fibers made via a process whereby a molten material (typically a polymer), is extruded under pressure through orifices in a spinneret or die. High velocity hot air impinges upon and entrains the filaments as they exit the die to form filaments that are elongated and reduced in diameter and are fractured so that fibers of generally variable but mostly finite lengths are produced. This differs from a spunbond process whereby the continuity of the filaments is preserved along their length. An exemplary meltblown process may be found in U.S. Pat. No. 3,849,241 to Buntin et al.

As used herein, the term "nonwoven" means a porous, fibrous material made from continuous (long) filaments (fibers) and/or discontinuous (short) filaments (fibers) by processes such as, for example, spunbonding, meltblowing, carding, and the like. Nonwoven webs do not have a woven or knitted filament pattern.

As used herein, the term "spunbond fibers" refers to fibers made via a process involving extruding a molten thermoplastic material as filaments from a plurality of fine, typically circular, capillaries of a spinneret, with the filaments then being attenuated by applying a draw tension and drawn mechanically or pneumatically (e.g., mechanically wrapping the filaments around a draw roll or entraining the filaments in an air stream). The filaments may be quenched by an air stream prior to or while being drawn. The continuity of the filaments is typically preserved in a spundbond process. The filaments may be deposited on a collecting surface to form a web of randomly arranged substantially continuous filaments, which can thereafter be bonded together to form a coherent nonwoven fabric. Exemplary spunbond process and/or webs formed thereby may be found in U.S. Pat. Nos. 3,338,992; 3,692,613, 3,802,817; 4,405,297 and 5,665,300.

As used herein, the term "web" refers to an element that includes at least a fibrous layer or at least a film layer and has enough integrity to be rolled, shipped and subsequently processed (for example a roll of a web may be unrolled, pulled, taught, folded and/or cut during the manufacturing process of an article having an element that includes a piece of the web). Multiple layers may be bonded together to form a web.

While not intending to limit the utility of the stretchable laminate described herein, it is believed that a brief description of its characteristics as they may relate to the laminate manufacturing and intended use will help elucidate the invention. In heretofore stretchable laminates suitable for use, for example, as an element of an absorbent article, the laminates typically comprise at least a nonwoven web that is bonded to an elastic film. Modern absorbent articles such as diaper, pants or adult incontinence products include many elements that are at one time or another in contact with the caregiver or user's skin. The use of nonwoven materials is particularly advantageous in such elements due to the soft feel and their cloth-like appearance they provide. Modern disposable absorbent articles are also designed to provide an underwear-like fit. Some of the elements of modern absorbent articles are provided with elastic components which provide them with elastic properties and contribute not only to the performance but also the underwear-like fit of these absorbent articles when worn by a user. Non-limiting examples of such elements that include elastic components include ear panels of a diaper, side panels of a pant or at least part if not all of the outer cover. Known stretchable laminates typically include at least a nonwoven web that is bonded to an elastic film. The laminate is then mechanically activated to at least partially recover some of the ease of elongation that the elastic film had prior to being bonded to the nonwoven web. Mechanical activation of the stretchable laminate is often achieved by passing at least a portion of the laminate between a pair of pressure applicators having three-dimensional surfaces which at least to a degree are complementary to one another as disclosed, for example, in U.S. Pat. No. 5,167,897 to Weber et al., issued Dec. 1, 1992 and assigned to The Procter and Gamble Company. Typical stretchable laminates include an elastic film and two separate nonwoven webs that are respectively bonded on each side of the elastic film. Known nonwoven webs that have been used to make stretchable laminates are nonwoven webs made of carded staple fibers and nonwoven webs that include one or more layers of spunbond fibers such as a spunbond/meltblow/spunbond web. These carded or spunbond webs are made of mono-component fibers that are typically made of polypropylene. During mechanical activation, a carded web offers relatively little resistance to its elongation and, as a result, a stretchable laminate that includes such a carded web may be pre-strained or activated to a great extent without causing either the carded web or the elastic film to tear completely. However, carded webs can be rather costly in comparison to spunbond webs. On the other hand, spunbond webs tend to be much more difficult to elongate without causing the spunbond web and/or the elastic web to tear during the mechanical activation of the laminate. Since manufacturers of absorbent articles are under continuous pressure to reduce manufacturing cost and minimize manufacturing waste, it is believed that the stretchable laminate disclosed hereinafter may be a suitable alternative to already existing stretchable laminates. The foregoing considerations are addressed by the present invention, as will be clear from the detailed disclosures which follow.

Reference will now be made in detail to the present preferred embodiments of the invention, examples of which are illustrated in the accompanying drawings wherein like numerals indicate the same elements throughout the views and wherein reference numerals having the same last two digits (e.g., 20 and 120) connote similar elements.

In one embodiment of the invention schematically represented in FIG. 1, a stretchable laminate 10 comprises a nonwoven web 20 that is bonded to an elastic web 30 which form together a bi-laminate. The nonwoven web 20 comprises at least one layer 120 of spunbond fibers having top and bottom surface such that the bottom surface of the layer 120 is bonded to top surface or side of the elastic web 30 via an adhesive. The nonwoven web 20 may comprise additional layers such as for example at least one layer 220 of meltblown fibers (having top and bottom surfaces) and at least one layer 320 of spunbond fibers (also having top and bottom surfaces). The top surface of layer 220 faces the bottom surface of layer 320 and the top surface of layer 120 faces the bottom surface of layer 220. The layer 120 of spunbond fibers may have a basis weight of between 2 g/m$^2$ and 50 g/m$^2$, between 4 g/m$^2$ and 25 g/m$^2$ or even between 5 g/m$^2$ and 20 g/m$^2$. The layer 220 of meltblown fibers that may have a basis weight of between 0.5 g/m$^2$ and 10 g/m$^2$, between 0.5 g/m$^2$ and 8 g/m$^2$ or even between 1 g/m$^2$ and 5 g/m$^2$. The layer 320 of spunbond fibers may have a basis weight of between 2 g/m$^2$ and 50 g/m$^2$, between 4 g/m$^2$ and 25 g/m$^2$ or even between 5 g/m$^2$ and 20 g/m$^2$. The basis weight of any of the webs described herein may be determined using European Disposables and Nonwovens Association ("EDANA") method 40.3-90. The basis weight of any of the individual layers described herein, and which together form a web, may be determined by running in sequence each of the fiber forming beams that are used to form separate layers and then measuring the basis weight of the consecutive formed layer(s) according to EDANA method 40.3-90. By way of example, the basis weight of each of the layers of an spunbond/meltblown/spunbond web (comprising a first layer of spunbond fibers, a layer of meltblown fibers and a second layer of spunbond fibers) can be determined by first forming the first layer of spunbond fibers without forming the layer of meltblown fibers nor the second layer of spunbond fibers. The nonwoven that is produced includes only the first layer of spunbond fibers and its basis weight can be determined according to EDANA method 40.3-90. The basis weight of the layer of meltblown fibers can be determined by forming the first layer of spunbond fibers under the same conditions as in the previous step followed by formation of the layer of meltblown fibers laid on top of the first layer of spunbond fibers. The aggregate basis weight of the spunbond/meltblown web (which is again formed of the first layer of spundbond fibers and the layer of meltblown fibers) can be determined according to EDANA method 40.3-90. Since the basis weight of the first layer of spunbond fibers is known, the basis weight of the layer of meltblown fibers can be determined by subtracting the value of the basis weight of the first layer of spunbond fibers from the value of the aggregate basis weight of the spunbond/meltblown web. The basis weight of the second layer of spunbond fibers can be determined by forming the first layer of spunbond fibers and the layer of meltblown fibers under the same conditions as in the previous step followed by the formation of the second layer of spunbond fibers laid on top of the layer of meltblown fibers. The aggregate basis weight of the spunbond/meltblown/spunbond web can be determined according to EDANA method 40.3-90. Since the basis weight of the spunbond/meltblown web is known, the basis weight of the second layer of spunbond fibers can be determined by subtracting the value of the aggregate basis weight of the spunbond/meltblown web from the value of the aggregate basis weight of the spunbond/meltblown/spunbond web. The foregoing steps used to determine the basis weight of individual layers forming a web can be applied on as many layers as the ultimate nonwoven web includes. As previously discussed, the aggregate basis weight of the nonwoven web 20 is equal to the sum of the basis weight of each of its individual layers. In one embodiment represented in FIG. 2, it can be advantageous to provide the nonwoven web 20 with at least two layers 1120, 2120 of spunbond fibers (each having top and bottom surfaces) in the portion of the web 20 that is disposed on the elastomeric web facing portion of the nonwoven web 20 (i.e. the portion of the nonwoven web located between the layer 220 of meltblown fibers and the elastic web 30) instead of a single layer 120 of spunbond fibers. It is believed that the at least two separate layers of spunbond fibers may have a combined basis weight equal to the basis weight of the layer 120 of spunbond fibers and provide a greater level of performance than this single layer 120 during activation of at least a portion of the stretchable laminate. It is also believed that the at least two separate layers of spunbond fibers may have a combined basis weight that is less than the basis weight of a single layer 120 of spunbond fibers and provide the same level of performance as the single layer 120. By way of example, each of the layers of spunbond fibers 1120 and 2120 may have a basis weight of 6 g/m$^2$ as opposed to a single layer of spunbond fibers having a basis weight of at least 12 g/m$^2$. Each of the layers 1120 and 2120 of spunbond fibers may have a basis weight of between 1 g/m$^2$ and 25 g/m$^2$, between 2 g/m$^2$ and 12.5 g/m$^2$ or even between 2.5 g/m$^2$ and 10 g/m$^2$. It is believed that at least two separate layers of spunbond fibers provide greater basis weight homogeneity to the nonwoven web 20 and in particular to the elastomeric web facing portion of the nonwoven web 20. Without intending to be bound by any theory, it is also believed that since the elastomeric web facing portion of the nonwoven web 20 is the portion of the web that is directly bonded to the elastomeric web, a more homogeneous basis weight may help prevent local micro-tearing of the nonwoven web 20 during mechanical activation which may propagate to the elastomeric web and cause the elastomeric web 30 to tear. It is believed that local micro-tearing of the nonwoven web during mechanical activation may lead to an over-elongation of the portion of the elastomeric web that is in the immediate vicinity of the micro-tear formed on the nonwoven web. This over-elongation of the elastomeric web may result in the elastomeric web being torn or ruptured, in particular when the elastomeric web is a film. It should be understood that the elastomeric web facing portion of the nonwoven web 20 may include more than two layers of spunbond fibers with an even lower basis weight to provide an even greater homogeneity.

In one embodiment, it can also be advantageous to provide the nonwoven web 20 with at least two layers 1220, 2220 of meltblown fibers (each having top and bottom surfaces) in the central portion of the web 20 instead of a single the layer 220 of meltblown fibers. The at least two separate layers 1220, 2220 of meltblown fibers may have a combined basis weight equal to the basis weight of the layer 220 of meltblown fibers and provide a greater level of performance than this single layer 120. In the alternative, the at least two separate layers of meltblown fibers may have a combined basis weight that is less than the basis weight of a single layer 220 of meltblown fibers and provide the same level of performance as the single layer 220. By way of example, each of the layers of meltblown fibers 1220 and 2220 may have a basis weight of 1 $g/m^2$ as opposed to a single layer of meltblown fibers having a basis weight of at least 2 $g/m^2$. Each of the layers 1220 and 2220 of meltblown fibers may have a basis weight of between 0.25 $g/m^2$ and 5 $g/m^2$, between 0.25 $g/m^2$ and 4 $g/m^2$ or even between 0.5 $g/m^2$ and 2.5 $g/m^2$. A layer 220 of meltblown fibers may be particularly advantageous when the layer 120 or layers 1120, 2120 of spunbond fibers disposed in the elastomeric web facing portion of the web 20 are adhesively bonded to the elastomeric web 30 with for example a hotmelt adhesive (schematically represented by round dots 15 in FIGS. 1 and 2). It is believed that a meltblown layer 220 may prevent the adhesive from reaching and even "bleeding though" the layer of spunbond fibers 320 which is the layer that may be in contact with the caregiver or user's skin. It is believed that two separate layers of meltblown fibers having a low basis weight are more effective at preventing adhesive "bleed-through" than a single layer of meltblown fibers having a higher basis weight. It is also believed that a layer 220 of meltblown fibers may conveniently be used as a "carrier layer" for additional smaller fibers such as nanofibers (i.e. fibers having a diameter of less than 1 μm). It is further believed that a layer 220 of meltblown fibers having a homogeneous basis weight may help achieve a more uniform coverage of any coating applied to the nonwoven web such as an adhesive coating, a printed ink, a surfactant and/or a softening agent. It should be understood that the central portion (i.e. the portion of the web disposed between the outer layers of the web) of the nonwoven web 20 may include more than two layers 1220, 2220 of meltblown fibers with an even lower basis weight in order to provide an even greater homogeneity. One of ordinary skill will also appreciate that although the production of each of the layers 1120, 2120 of spunbond fibers and each or the layers 1220 and 2220 may require separate beams, it is believed that the production throughput of the nonwoven web may be increased. In the embodiment represented in FIG. 2, the top surface of layer 1120 faces the bottom surface of layer 2120, the top surface of layer 2120 faces the bottom surface of layer 1220, the top surface of layer 1220 faces the bottom surface of layer 2220 and the top surface of layer 2220 faces the bottom surface of layer 320.

In one embodiment, it can be also advantageous to provide the nonwoven web 20 with at least two layers of spunbond fibers in the portion of the web 20 that is facing away from the elastic web 30 (i.e. the portion of the nonwoven web positioned on top of the layer 220 of meltblown fibers) instead of a single the layer 320 of spunbond fibers.

In one embodiment, the elastomeric web 30 may be an elastomeric nonwoven web or an elastomeric film. The elastic web 30 in the form of a film may include a core layer 130 made of an elastomeric material that may be directly bonded to the spunbond layer 120 of the nonwoven web 20. A core layer 130 can be directly bonded to the nonwoven web 20 by extruding an elastomeric material directly onto a nonwoven web. An adhesive may be added onto the contact surface of the extruded elastomeric material to increase the bond strength between the elastomeric web and the nonwoven web. Non-limiting examples of suitable elastomeric materials include thermoplastic elastomers chosen from at least one of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXXPOL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del. Other particularly suitable examples of elastomeric materials include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518,378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher α-olefin) incorporated into the backbone. Suitable elastomeric RCP materials are available under the names VISTAMAXX (available from ExxonMobil, Houston, Tex.) and VERSIFY (available from Dow Chemical, Midland, Mich.).

It will be appreciated that elastomeric materials that are typically used to form an elastic film may be tacky and cause the elastic film to stick to itself in the event the elastic film is rolled. It may be beneficial to provide at least one of the surfaces or sides of the core layer 130 with at least a skin layer 230 made of a material that does not stick to itself. Non-limiting examples of suitable materials for use as a skin layer include polyolefins such as polyethylene. Among other benefits, a skin layer 230 allows the elastic film 30 to be rolled for shipping and later unrolled for further processing. In one embodiment, the elastic film 30 may include a second skin layer disposed on the other surface or side of the core layer 130. The elastic film web may have a basis weight of between 10 $g/m^2$ and 150 $g/m^2$, between 15 $g/m^2$ and 100 $g/m^2$ or even between 20 $g/m^2$ and 70 $g/m^2$. The core layer 130 of the elastic film may have a basis weight of between 10 $g/m^2$ and 150 $g/m^2$, between 15 $g/m^2$ and 100 $g/m^2$ or even between 20 $g/m^2$ and 70 $g/m^2$ and the skin layer 230 (if present) may have a basis weight of between 0.25 $g/m^2$ and 15 $g/m^2$, between 0.5 $g/m^2$ and 10 $g/m^2$ or even between 1 $g/m^2$ and 7 $g/m^2$.

Figure 2:
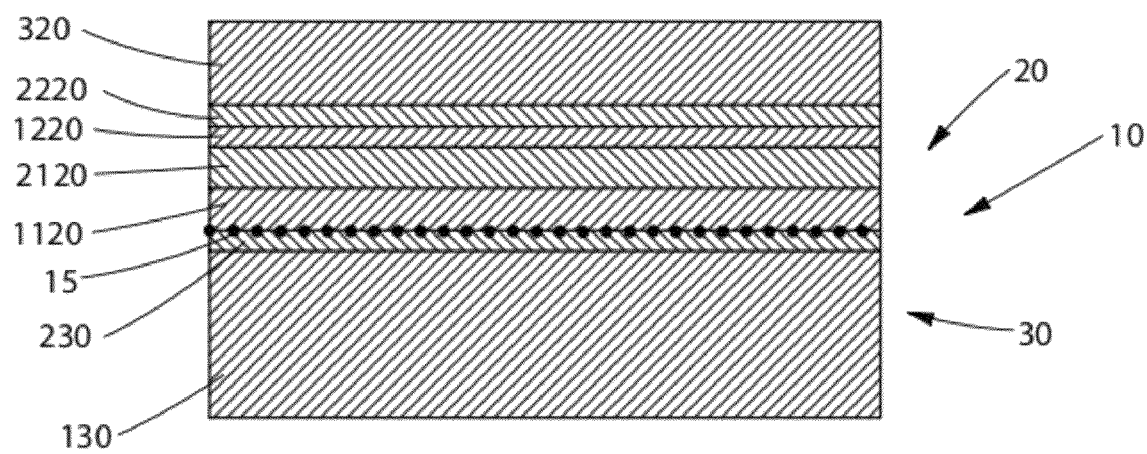
FIG. 2 is a schematic cross-sectional view of a stretchable laminate in accordance with another embodiment of the invention.
Figure 3:
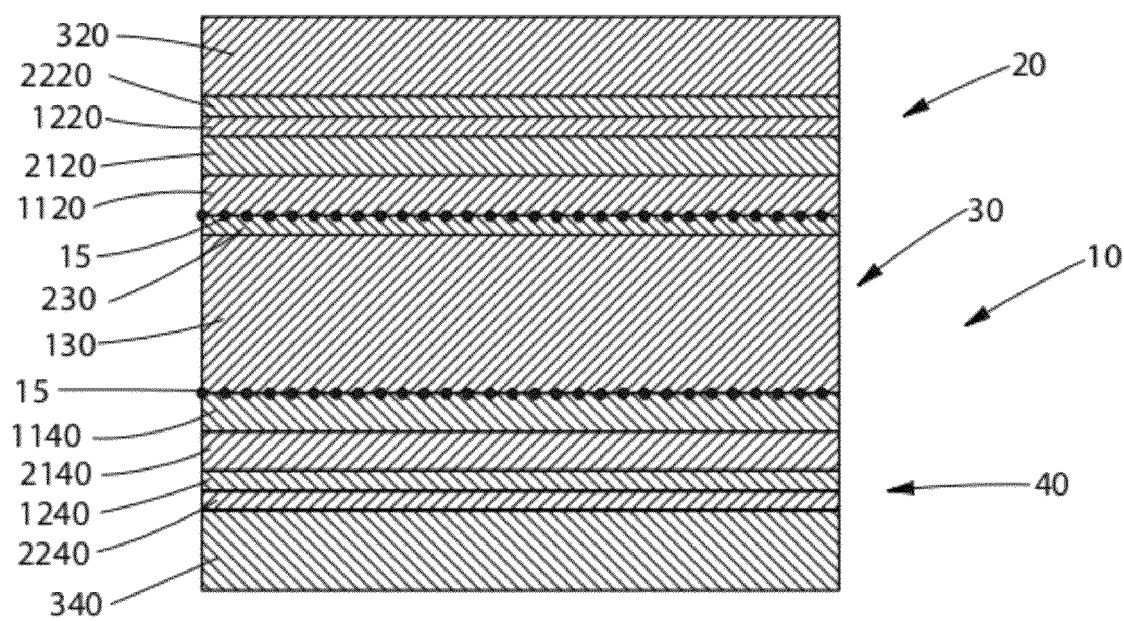
FIG. 3 is a schematic cross-sectional view of a stretchable laminate in accordance with another embodiment of the invention.

In one embodiment schematically represented in FIG. 3, the stretchable laminate previously discussed in the context of FIG. 2 may additionally comprise a second nonwoven web 40 bonded to the other surface or side of the elastic film 30. The second nonwoven web 40 may be a web of carded staple fibers or in the alternative a web comprising at least one layer of spunbond and/or meltblown fibers. In one embodiment, the second nonwoven web 40 can include any of the layers previously discussed in the context of the nonwoven web 20 (i.e. nonwoven layers identified by reference numerals 140, 240, 340, 1140, 2140, 1240 and 2240). Consequently, the elastomeric web facing portion of the second nonwoven web 40 can include one (140), two (1140, 2140) or more layers of spunbond fibers. The central portion of the second nonwoven web 40 can include one (240), two (1240, 2240) or more layers of meltblown fibers. In one embodiment, the nonwoven web 40 is bonded to the elastic film 30 such that it forms a mirror image of the nonwoven web 20 relative to the elastic film 30. As such, it can be advantageous (although not required) for each of the nonwoven webs 20 and 40 to be made of the same material and to include the same arrangement of layers in order to simplify the manufacturing process of the stretchable laminate.

Figure 4:
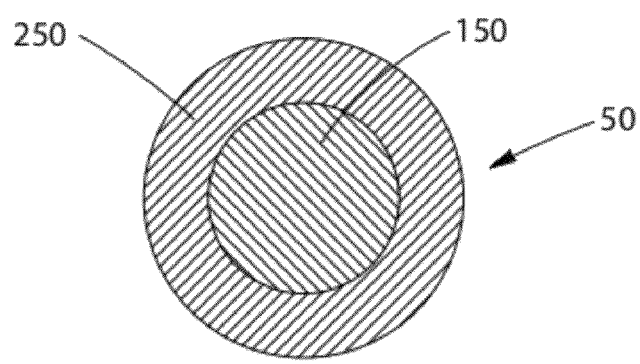
FIG. 4 is a schematic cross-sectional view of a bi-component fiber in accordance with an embodiment of the invention.

In one embodiment, any of the previously discussed nonwoven layers 120, 1120, 2120, 320, 140, 1140, 2140 and 340 of spunbond fibers can comprise or be made of bi-component fibers made of two polyolefin polymers having different melt temperatures and different tensile properties. In one embodiment, each of the two polyolefin polymers used to form the bi-component fibers are substantially non-elastic. Bi-component fibers may have any configuration known in the art but it is believed that bi-component fibers 50 as represented in FIG. 4 having a core 150 distinct from a sheath 250 may be advantageous in particular when the core 150 comprises a first polymer having a first melt temperature and the sheath 250 comprises a second polymer having a second melt temperature that is lower than melt temperature of the first polymer. In one embodiment, the melt temperature of the first polymer forming the core is at least 130° C., at least 140° C. or even at least 150° C. The melt temperature of the second polymer forming the sheath is less than 150° C., less than 140° C. or even less than 130° C. The melt temperature of a polymer may be determined according to ASTM D 3418. In one embodiment, the first polymer forming the core may have a density of at least 0.9 g/cc, at least 0.92 g/cc or at least 0.95 g/cc. The second polymer forming the sheath may have a density of less than 0.95 g/cc, less than 0.92 g/cc or less than 0.9 g/cc. The density of a polymer may be determined according to ASTM D 792.

Figure 5A:
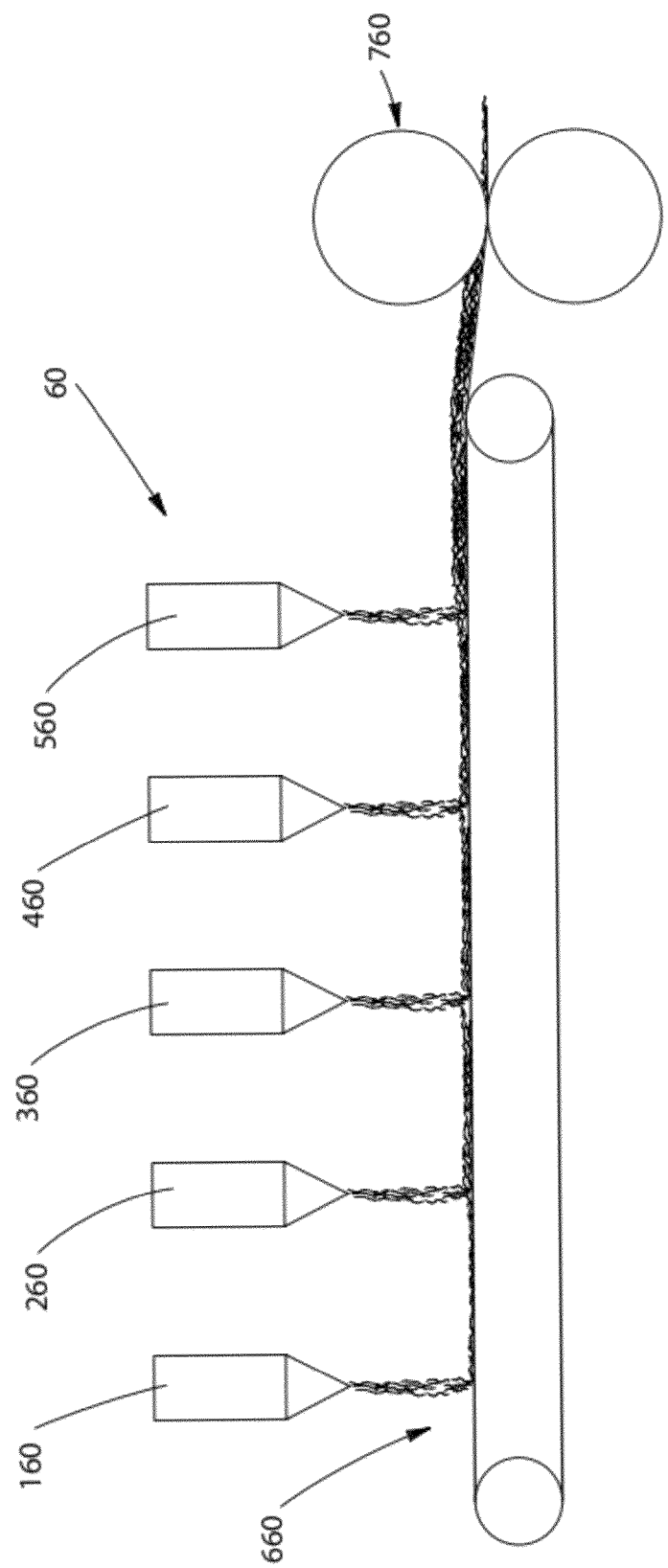
FIG. 5A is a schematic representation of a nonwoven web manufacturing process.
Figure 5B:
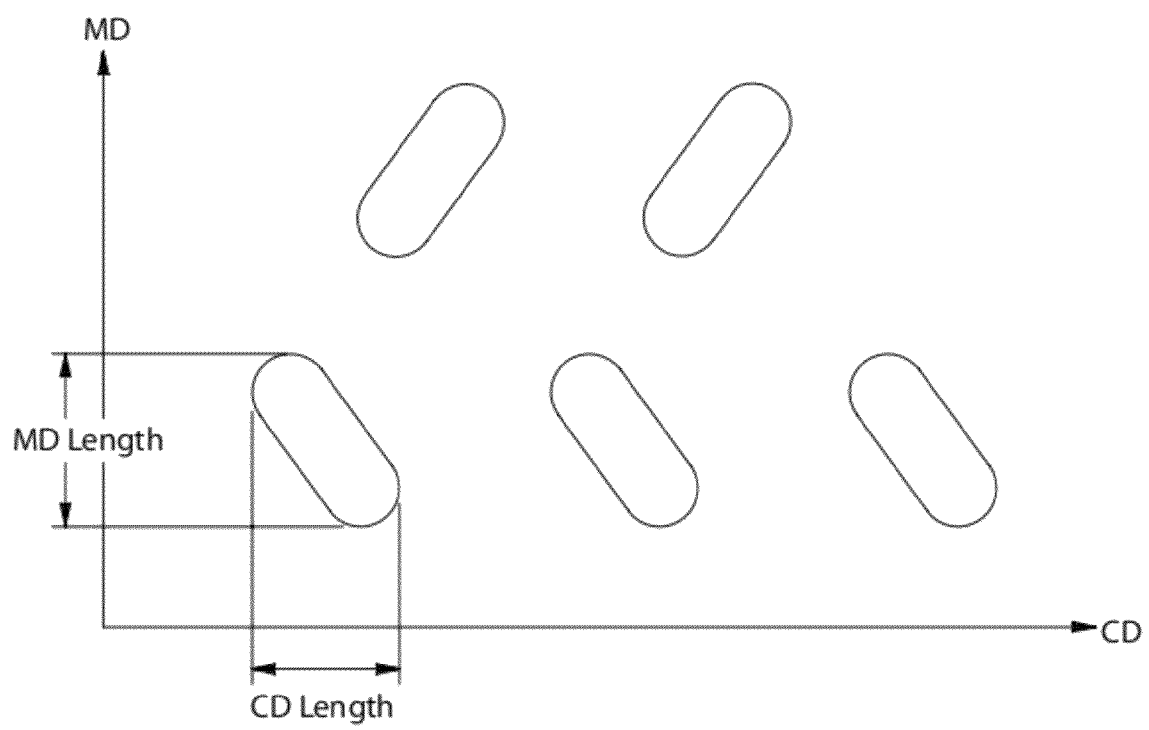
FIG. 5B is a schematic representation of a pattern of thermo-bonds formed on a nonwoven web.

A process line 60 that may be used to manufacture a nonwoven web including two layers of bi-component spunbond fibers, two layers of meltblown fibers and one layer of spunbond fibers is schematically represented in FIG. 5. The process line includes a first beam 160 that is adapted to produce bi-component spunbond fibers, a second beam 260 and a third beam 360 that are adapted to produce meltblown fibers and fourth and fifth beams 460, 560 that are adapted to produce bi-component spunbond fibers. Each of the beams 160, 460 and 560 that are used to produce bi-component fibers may be connected to a pair of extruder (not shown) that feed the respective polymers (forming the core and the sheath of the fibers) to spinnerets of the beams as it is well know in the art. It will be appreciated that various spinneret configurations may be used to obtain different bi- or multicomponent fibers. The bi-component spunbond fibers that are produced by the first beam 160 are deposited on a forming surface 660 which can be a foraminous belt. The forming surface 660 may be connected to a vacuum in order to draw the fibers onto the forming surface. The meltblown fibers that are produced by the second beam 260 are then deposited onto the first layer of bi-component spunbond fibers. The fibers of each subsequent beam are deposited onto the layer formed by the preceding beam. The resulting web of five layers may then be thermo point bonded with a pair of rollers 760 as it is well know in the art. It will also be appreciated that the number, the order of the beams and the type of fibers produced by each beam may be adjusted as needed to produce a desired multi-layers nonwoven web. When meltblown fibers are laid onto a first (or even a second) layer of spunbond fibers, some of the meltblown fibers are deposited into the interstices formed by the much larger spunbond fibers and some fibers are even able to reach the side of the spunbond layer that is resting on top of the forming surface through these interstices. When such an SMS includes at least a layer of spunbond bi-component fibers having a sheath made for example of polyethylene and at least a layer of meltblown fibers made for example of polypropylene, it is observed that the meltblown fibers extending through the interstices of the first layer of spunbond fibers (i.e. the layer laid directly on the forming surface) may easily be removed when this side of the nonwoven SMS web is rubbed against another surface. The removal of these fibers may result in various problems depending on which side of the SMS is ultimately the most likely to be subject to rubbing against another surface. For example, an adhesive may be applied directly onto one of the sides of an SMS web in order to bond the SMS web to another web. One suitable process to apply an adhesive directly onto the web is slot coating. In a slot coating process, a side of a web is moved against a die which includes one or more openings through which a molten hotmelt adhesive is delivered. The molten hotmelt adhesive can cause the die to reach a relatively elevated temperature which can at least soften or even melt the polyethylene sheath of the spunbond fibers. In addition, the continuous rubbing of the nonwoven web against the die can cause the meltblown fibers protruding through the interstices of the first spunbond layer to break and to accumulate against the die when the exterior surface of this layer is rubbed against the die. This accumulation of meltblown polypropylene fibers in combination with the presence of soften or even molten polyethylene can lead to frequent interruptions of the manufacturing process (in order to clean the die) and waste of material. It will be appreciated that such an issue may not occur when the fibers forming the meltblown layer and the sheath of the bi-component fibers forming the spunbond layer include a similar polymer such as a polypropylene. When a slot coating process is used, it can therefore be advantageous to apply an adhesive directly on the exterior facing surface of the spunbond layer that has been formed last during the web manufacturing process (i.e. the layer that includes no or very little meltblown fibers protruding through interstices of a spunbond layer). In another embodiment, a hotmelt adhesive having a lower melt and application temperature may be used to help lower the temperature of the die during the slot coating process. Lowering the temperature of the die below the melt temperature of polyethylene used to make the sheath of the bi-component fibers, reduces the chances that the polyethylene sheath may melt during the slot coating process. In an alternative embodiment, a high or low melt temperature adhesive may be applied on the exterior facing surface of either the first or last spunbond layer formed during the web manufacturing process, via a direct (i.e. direct contact between the application tool and the web surface) but low-rubbing application process. By "low-rubbing application process," it is meant a process where at least a portion of the application and the web are in motion during application of the adhesive in order to minimize the rubbing of the web against the application tool. One example of such a process include printing the adhesive onto the web with gravure roll as disclosed in U.S. Pat. No. 6,531,025 to Lender et al., issued Mar. 11, 2003 and assigned to The Procter & Gamble Company. In yet another embodiment, a high or low melt temperature adhesive may be applied on the exterior facing surface of either the first or last spunbond layer formed during the web manufacturing process, via an indirect (i.e. no direct contact between the application tool and the web surface) application process. A suitable example of such a process includes spraying the adhesive onto the web.

Figure 6:
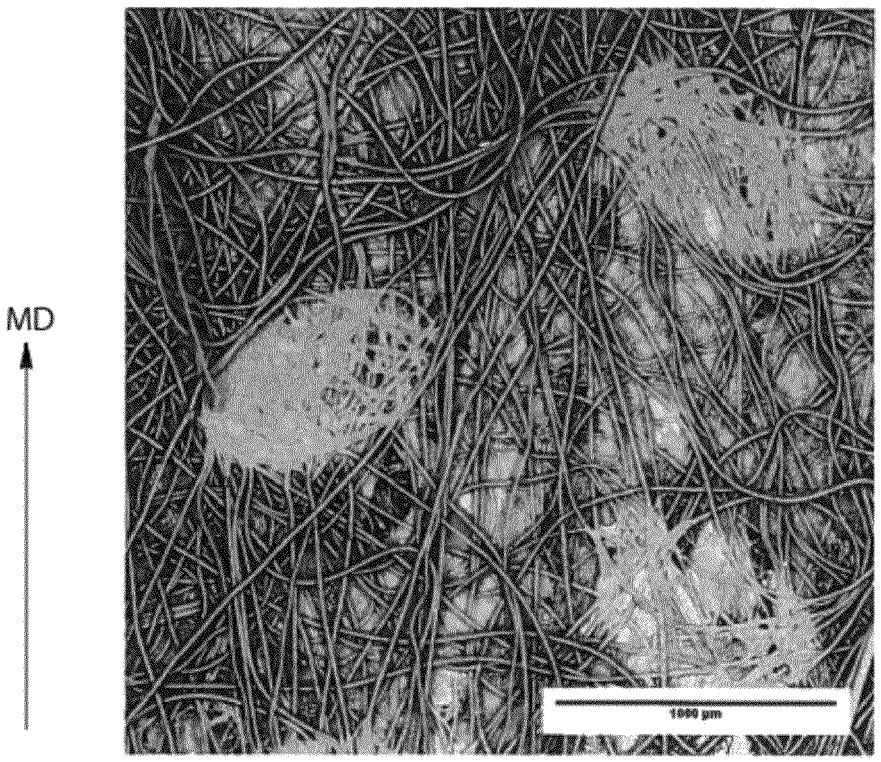
FIG. 6 is a photograph of a stretchable laminate before mechanical activation.
Figure 7:
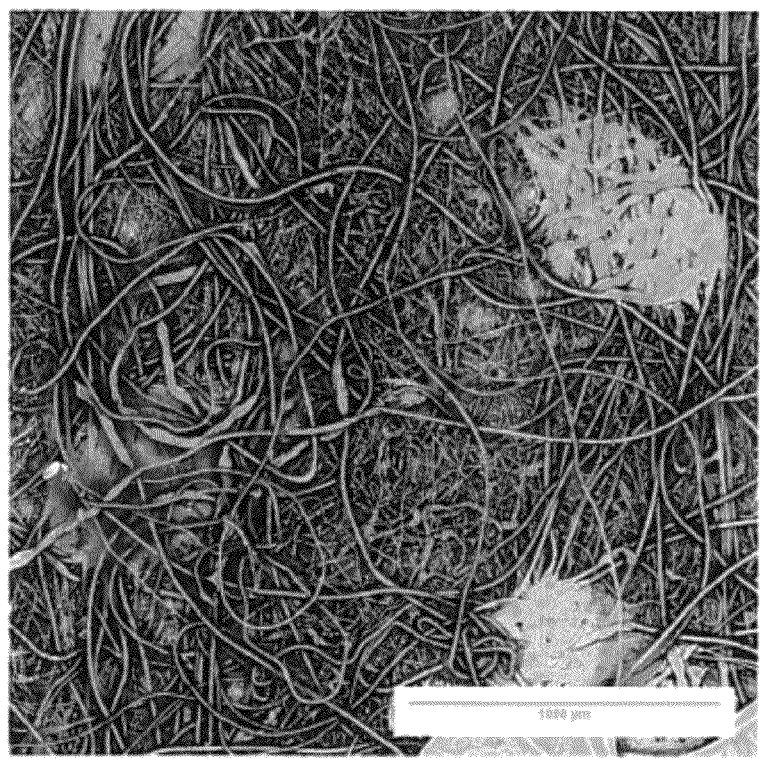
FIG. 7 is a photograph of a stretchable laminate after mechanical activation.
Figure 8:
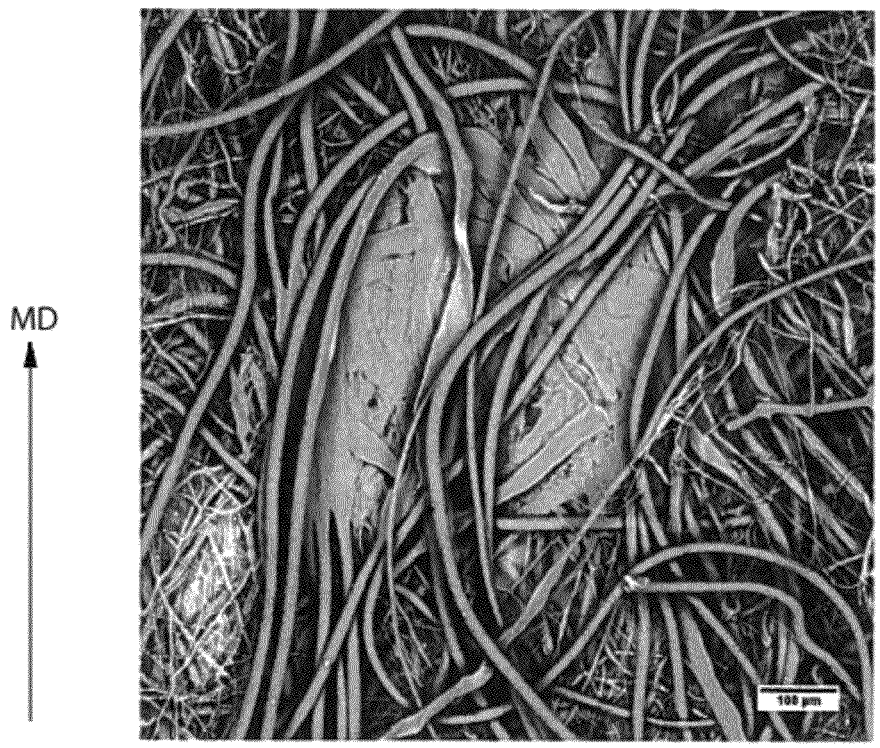
FIG. 8 is a magnified photograph of a bond site of a stretchable laminate after mechanical activation.
Figure 9:
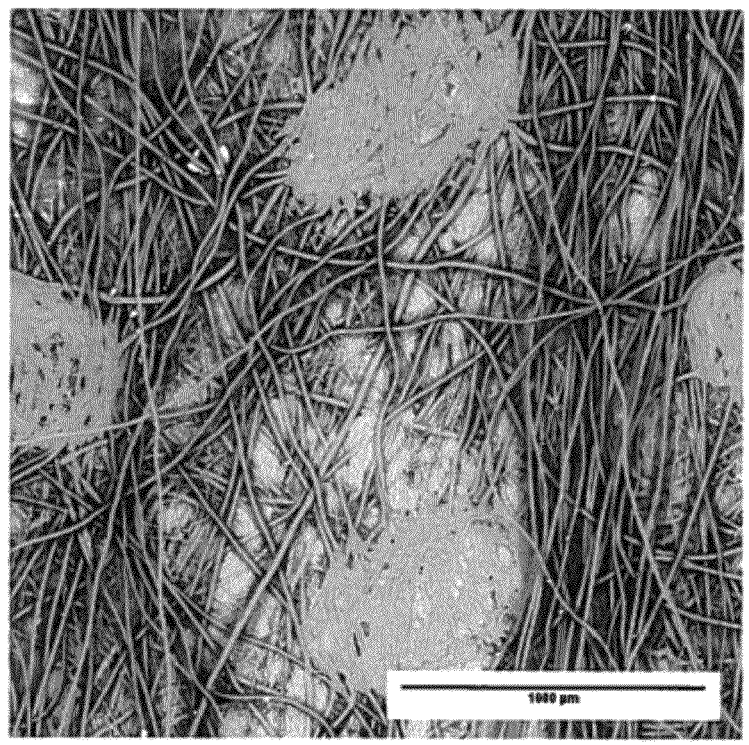
FIG. 9 is a photograph of a stretchable laminate in accordance with an embodiment of the invention before mechanical activation of the laminate.
Figure 10:
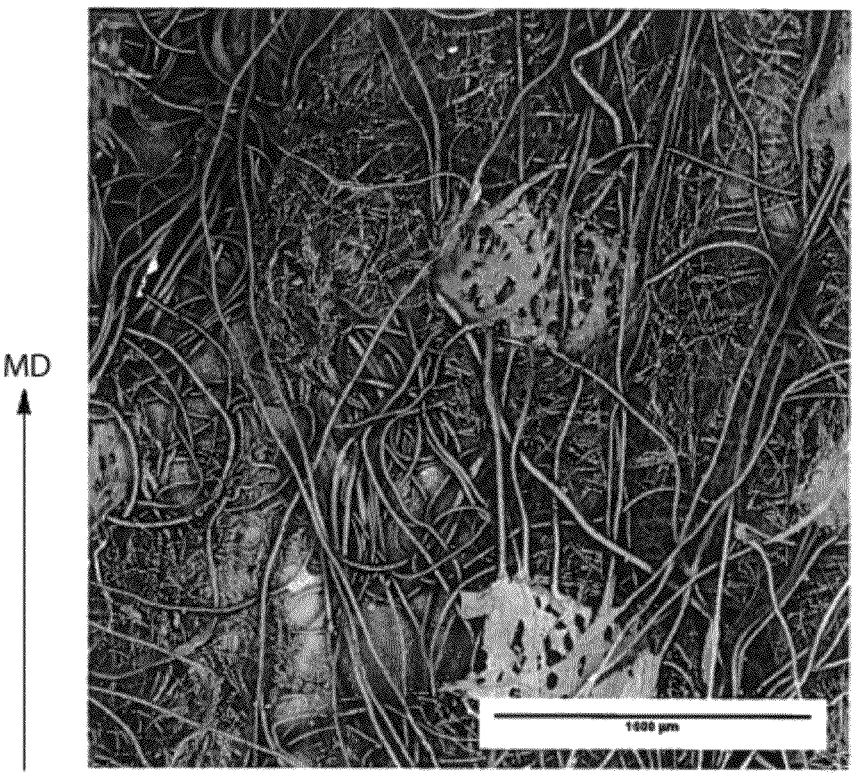
FIG. 10 is a photograph of a stretchable laminate in accordance with an embodiment of the invention after mechanical activation of the laminate.
Figure 11:
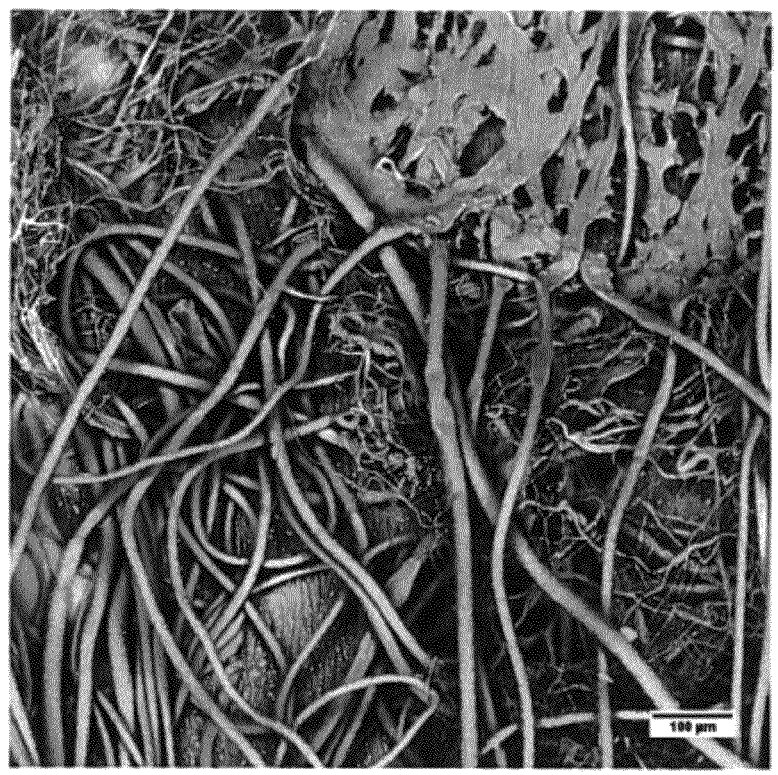
FIG. 11 is magnified photograph of a bond site of a stretchable laminate in accordance with an embodiment of the invention after mechanical activation of the laminate.

As previously discussed, at least one of the layers (that include bi-component fibers) of a nonwoven web may be adhesively bonded to the elastomeric web with for example a hotmelt adhesive. In one embodiment, a hotmelt adhesive is applied directly onto the nonwoven web at a temperature that is less than the melt temperature of the polymer that forms the sheath of the bi-component fibers. In one embodiment, a hotmelt adhesive is applied in a molten/liquid phase at a temperature of less than 150° C., less than 140° C. or even less than 130° C. such that the molten adhesive does not cause the polymer that forms the sheath of the fibers to melt significantly. Non-limiting examples of hotmelt adhesive that can be applied in a molten/liquid phase at such temperatures are disclosed in US Patent Application Publication No. 2007/0088116 to Abba et al. filed Oct. 14, 2005, published Apr. 19, 2007, and assigned to Bostik, Inc. 11320 Watertown Plank Road, Wauwatosa, Wis. 53226. However, it may also be advantageous to apply an adhesive indirectly to the nonwoven web (i.e. without direct contact of the application tool against the nonwoven web) at a temperature that is higher than the melt temperature of the polymer forming the sheath as long as the temperature of the adhesive is less than the melt temperature of the polymer forming the sheath of the fibers once the adhesive reaches the fibers of the web. It is believed that under such conditions, the adhesive does not cause the sheath of the fibers to melt significantly. In an alternative embodiment, it may be advantageous to apply an adhesive onto the nonwoven web at a temperature that is higher than the melt temperature of the polymer forming the sheath of the bi-component fibers. The adhesive may be applied at temperature of at least 130° C., at least 140° C. or even at least 150° C. Non-limiting examples of such hotmelt adhesive include ZEROCREEP that is available from Bostik. It is believed that when a hotmelt adhesive is applied to the nonwoven at a temperature that is higher than the melt temperature of the polymer forming the sheath of the bi-component fibers, the sheath may melt and increase the number of bonds between individual fibers and between the fibers and the skin layer of an elastomeric web especially when the composition of the skin layer comprises is substantial the same as the composition of the polymer forming the sheath. In one embodiment, any of the layers of spunbond fibers previously discussed in the context of a nonwoven web 20 and/or 40, may comprise bi-component fibers of the core/sheath type such that the core of these fibers comprises a polypropylene polymer and the sheath of these fibers comprises a polyethylene polymer. Nonwoven webs are typically thermo point bonded to provide the web with enough integrity to be rolled and further processed at a later time. One suitable example of a thermo point bonding process includes calendering using calender rolls with a bonding pattern. During the calendering process, bonds are formed on or through the web by locally applying pressure and heat to cause the polymer of the fibers to flow within the bond region. However, it is believed that the calendering temperature of any of the previously described nonwoven webs that includes a layer of spunbond bi-component fibers should be greater than the melt temperature of the polymer forming the sheath of the fibers but that it should also be lower than the melt temperature of the polymer forming the core of those fibers. It is believed that a calendering temperature greater than the melt temperature of both the polymers forming the bi-component fibers may have an adverse impact on the tensile properties of the nonwoven web in particular when the nonwoven web includes core/sheath type bi-component fibers. It is believed that when the calendering temperature of a bi-component fiber web is greater than the melt temperature of both the polymers forming the bi-component fibers, these fibers are weakened in the vicinity of the thermo-bonds and that, as a result, such a nonwoven web may be more prone to localize tearing during mechanical activation which may also result in the elastic film being torn as well. In one embodiment, any of the nonwoven webs disclosed herein that include bi-component fibers are thermo point bonded at between 110° C. and 140° C., between 115° C. and 135° C. or even between 120° C. and 130° C. In contrast, when the calendering temperature of a bi-component fiber web is less than the melt temperature of the polymer forming the core but is higher than the melt temperature of the polymer forming the sheath of the bi-component fibers, the core of these fibers maintain a sufficient level of strength which allows the web to elongate to a greater extent with a reduced chance of catastrophic failure of the nonwoven web during mechanical activation of a laminate. FIGS. 6 through 11 are pictures of two nonwoven webs and are taken with an electron microscope. FIG. 6 is a picture of a spunbond/meltblown/spunbond nonwoven web whose fibers are made of a mono-component polypropylene and that has been calendered at a temperature higher than the melt temperature of the polypropylene used to make the fibers of the web. The nonwoven web of FIG. 6 is bonded to an elastic film that is not visible on this picture. Three bond sites are visible on this picture. FIG. 7 is a picture of the same nonwoven web of FIG. 6 in an area of the web that has been mechanically activated. Four bond sites are at least partially visible on this picture. The left side of the picture includes two bond sites that have been strained during mechanical activation of the laminate. Several of the spunbond fibers have "popped out" of the bond site they were part of prior to mechanical activation as can be seen in FIG. 8 which is a magnified picture of one of the bond sites shown in FIG. 7. Some of these fibers have even been broken during mechanical activation. FIG. 9 is a picture of a spunbond/meltblown/spunbond nonwoven web whose fibers are made of polypropylene/polyethylene bi-component fibers of the core/sheath type that has been calendered at a temperature higher than the melt temperature of the polyethylene but lower than the melt temperature of the polypropylene used to make the fibers of the spunbond layers. The nonwoven web of FIG. 9 is bonded to an elastic film that is not visible on this picture. FIG. 10 is a picture of the same spunbond/meltblown/spunbond nonwoven web as in FIG. 9 in an area of the nonwoven web that has been subjected to mechanical activation. The elastic film of the laminate is at least partially visible in the left portion of the picture. Although the bond sites visible in FIG. 10 appear to have been deformed or strained during mechanical action, very few of the bi-component spunbond fibers have "popped out" of the bond sites. In addition, very few of these fibers appear to have been broken during mechanical activation. FIG. 11 is a magnified picture of one of the bond sites of the nonwoven web of FIG. 10. The molten polyethylene sheath is at least partially visible in this picture. It should be noted that the nonwoven web represented in FIGS. 6 through 8 is disposed on one side of an elastic film and that the nonwoven web represented in FIGS. 9 through 11 is disposed on the other side of the elastic film to form a stretchable laminate.

To further illustrate the benefit of a nonwoven web that includes layers of spunbond bi-component fibers in comparison to a nonwoven web that includes layers of spunbond mono-component fiber, the tensile curve of different samples of nonwoven webs is measured in the cross-machine direction of the webs.

Figure 12:
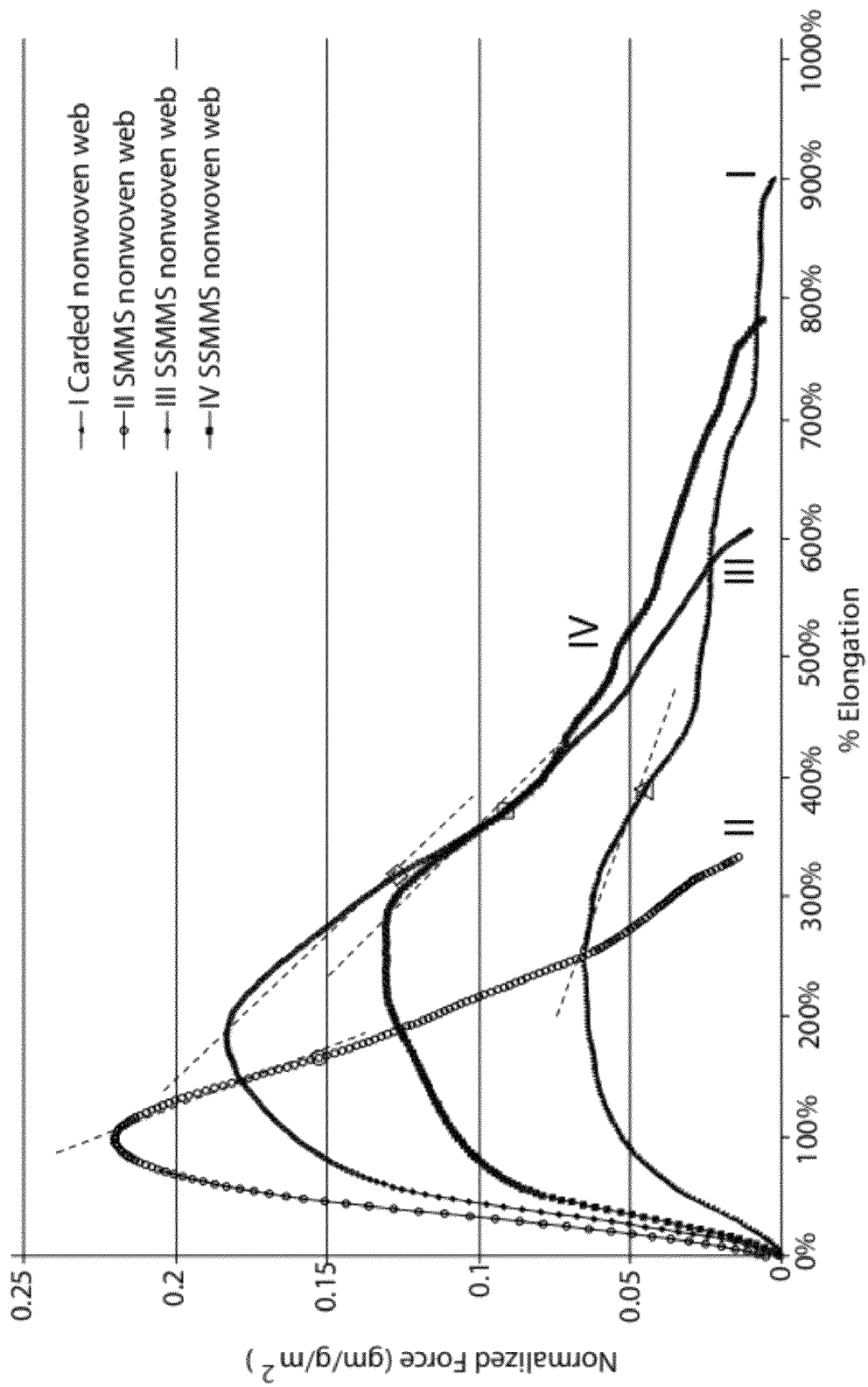
FIG. 12 represents tensile curves for various nonwoven webs.

Pre-Activation Tensile Test:

A first tensile test that is intended to mimic the behavior of a nonwoven web during mechanical activation in the CD direction of a laminate is performed on several nonwoven webs. This test is done following EDANA method 20.2-89 with the following changes. A specimen measuring 10 mm (along the CD of the web) by 25 mm (along the MD of the web) of a given nonwoven web is delicately cut from the web. The tensile curve of this specimen is obtained by gripping the edges parallel to the Machine Direction of the specimen with clamps connected to a tensile tester such as a tester from MTS. The gauge length (i.e. clamp to clamp separation) is approximately 5 mm. The tensile curve is obtained at a crosshead displacement speed of approximately 2 mm/s. In order to minimize the influence of the basis weight of each web sample being tested, each curve is normalized for the basis weight of the sample being tested (i.e. the values of the force applied are divided by the value of the aggregate basis weight of the web sample being tested). The elongation of each sample is reported on the x axis in percent elongation while the force applied to each sample is reported on the y axis in Newton per centimeter grams (N·m$^2$/g·cm). The specimen is pulled until it ruptures (i.e. the post peak force response reaches a value less than 10% of the peak force). Results of the tensile tests are represented in FIG. 12.

The tensile curve indicated by Roman numeral I is obtained on a nonwoven web made of carded staple fibers having an average diameter of 18.4 microns and having an aggregate basis weight of 27 g/m$^2$. Such a carded nonwoven web is commercially available from Albis Germany Nonwoven GmbH, Aschersleben Del. The tensile curve indicated by Roman numeral II is obtained on a SMMS nonwoven web made of mono-component polypropylene fibers and having an aggregate basis weight of 17 g/m$^2$. The fibers of the first and second spunbond layers have an average diameter of 19 microns and each have a basis weight basis weight of 7.25 g/m$^2$. The fibers of each of the two layers meltblown layers of this web have an average diameter of 2.4 microns and each meltblown layer has a basis weight of 1.25 g/m$^2$. Such a SMMS nonwoven web is commercially available from Fibertex, from Aalborg Denmark. The tensile curve indicated by Roman numeral III is obtained on a SSMMS nonwoven web whose spunbond layers are made of bi-component polypropylene/polyethylene fibers of the core/sheath type and having an aggregate basis weight of 20 g/m$^2$. The fibers of each of the layers of spunbond bi-component fibers have an average diameter of 19.0 microns and each of these layers has a basis weight of 6 g/m$^2$. The ratio of polypropylene to polyethylene of the bi-component fibers is approximately 70/30 by weight. The fibers of each of the two layers meltblown fibers of this web have an average diameter of 2.6 microns and each meltblown layer has a basis weight of 1 g/m$^2$. This SSMMS nonwoven web is provided by Pegas Nonwovens s.r.o., Znojmo CZ. The tensile curve indicated by Roman numeral IV is obtained on a SSMMS nonwoven web whose spunbond layers are made of bi-component polypropylene/polyethylene fibers of the core/sheath type and having an aggregate basis weight of 20 g/m$^2$. The fibers of each of the layers of spunbond bi-component fibers have an average diameter of 20.0 microns and each of these layers has a basis weight of 6 g/m$^2$. The ratio of polypropylene to polyethylene of the bi-component fibers is approximately 70/30. The fibers of each of the two layers meltblown layers of this web have an average diameter of 2.6 microns and each meltblown layer has a basis weight of 1 g/m$^2$. This SSMMS nonwoven web is provided by Pegas. The tensile curve of the carded nonwoven web indicates that this web does not require a lot of force to be elongated (the maximum force peaks at approximately 6.6 10 E-2 Nm$^2$/gcm for an elongation of approximately 250% in the sample tested) and it maintains most of its integrity even at a high elongation (the sample tested is able to elongate 900% its original length). The SMMS nonwoven web that includes mono-component fibers of polypropylene requires a much greater amount of force to be elongated (the maximum force peaks at approximately 22 10 E-2 Nm$^2$/gcm for an elongation of approximately 100% in the sample tested) and rapidly deteriorates (the sample tested is not able to sustain an elongation greater than about 330%). In contrast, the nonwoven webs that include layers of bi-component fibers maintain their integrity well past the maximum elongation obtained on a nonwoven web made of mono-component fibers. The maximum force applied to first of these nonwoven webs (that includes layers of bi-component spunbond fibers and is identified by Roman numeral III) peaks at approximately 18.5 10 E-2 Nm$^2$/gcm for an elongation of approximately 180% and this nonwoven web maintains most of its integrity even when it is elongated to approximately 500% of its original length. The maximum force applied to the second of these nonwoven webs (that also includes layers of bi-component spunbond fibers and is identified by Roman numeral IV) peaks at approximately 13 10 E-2 Nm$^2$/gcm for an elongation of approximately 270% and this nonwoven web maintains most of its integrity even when elongated to approximately 700% of its original length. In one embodiment, a stretchable laminate can include a nonwoven web that includes spunbond fibers which may be bi-component fibers as previously discussed, and which has a resistance to elongation of at least 5 10 E-2 Nm$^2$/gcm, at least 7.5 10 E-2 Nm$^2$/gcm or even 1 10

E-1 Nm²/gcm when a sample of this nonwoven web is elongated to 300% of its original length. In one embodiment, a stretchable laminate can include a nonwoven web that includes spunbond fibers which may be bi-component fibers as previously discussed, and which has a resistance to elongation of at least 5 10 E-2 Nm²/gcm when a sample of this nonwoven web is elongated to 300%, 400% or even 500% of its original length. It is believed that a nonwoven web having at least one of the previous characteristics is able to sustain mechanical activation in particular when a plurality of the portions of the stretchable laminate are subjected to an elongation higher than 300%.

It is observed that the tensile responses or curves of each of the nonwoven web samples all include a pre-activation maximum peak force (hereinafter "PA-MPF") or load after which the nonwoven webs start degrading or deteriorating. It is believed that the rate or "speed" at which a sample nonwoven web deteriorates after it has reached its PA-MPF may be a good indicator of the nonwoven web performance when bonded to an elastic film to form a stretchable laminate. One suitable way to determine the deterioration rate of a nonwoven web is to measure the slope of a straight line that connects the PA-MPF point on the curve to the point on the tensile curve representing a decrease in strain of approximately 30% after the PA-MPF. The absolute value of this slope is calculated in order to obtain a positive value. These lines are represented with dashed lines on FIG. 12 for the reader's convenience. The deterioration rate after a decrease in strain of approximately 30% (herein after $Dr_{30\%}$ of the nonwoven web made of carded staple fibers (indicated by Roman numeral I) is equal to approximately $$1.4\ 10E\text{-}2\ \left(\text{i.e.}\left|\frac{(0.046-0.066)}{(3.9-2.5)}\right|\right).$$

The $Dr_{30\%}$ of the nonwoven web made of a SMMS nonwoven web made of mono-component polypropylene fibers (indicated by Roman numeral II) is equal to approximately $$10.6\ 10E\text{-}2\ \left(\text{i.e.}\left|\frac{(0.15-0.22)}{(1.64-0.98)}\right|\right).$$

The $Dr_{30\%}$ of the SSMMS nonwoven web whose spunbond layers are made of bi-component polypropylene/polyethylene fibers of the core/sheath type (indicated by Roman numeral III) is equal to approximately $$4\ 10E\text{-}2\ \left(\text{i.e.}\left|\frac{(0.128-0.184)}{(3.2-1.8)}\right|\right).$$

The $Dr_{30\%}$ of the nonwoven web whose spunbond layers are made of bi-component polypropylene/polyethylene fibers of the core/sheath type (indicated by Roman numeral IV) is equal to approximately $$4.1\ 10E\text{-}2\ \left(\text{i.e.}\left|\frac{(0.09-0.131)}{(3.72-2.72)}\right|\right).$$

One of ordinary skill will appreciate that a nonwoven web having a relatively high $Dr_{30\%}$ value may tend to deteriorate rapidly after the web has been strained or elongated past its PA-MPF. Conversely, a nonwoven web having a relatively low $Dr_{30\%}$ value may tend to maintain its integrity after the web has been strained or elongated past its PA-MPF. In one embodiment, a stretchable laminate includes an elastic film and at least a nonwoven web bonded to one side of this film and which comprises at least one layer of spunbond fibers, preferably bi-component fibers, having a $Dr_{30\%}$ of less than 10 10 E-2. This nonwoven web may also have a $Dr_{30\%}$ of less than 8 10 E-2, less than 6 10 E-2, or even less than 5 10 E-2. In one embodiment, it may be advantageous for this nonwoven web to have a $Dr_{30\%}$ of between 1 10 E-2 and 10 10 E-2, between 2 10 E-2 and 8 10 E-2, or even between 3 10 E-2 and 6 10 E-2, It is worth noting that although the aggregate basis weight of the nonwoven webs that include bi-component spunbond fiber (indicated by Roman numerals III and IV) is higher than the basis weight of the nonwoven web that is made of mono-component spunbond fibers, their PA-MPF is surprisingly lower than the PA-MPF of the nonwoven web that is made of mono-component spunbond fibers. It is also worth noticing that the nonwoven webs that include bi-component spunbond fibers reach their respective PA-MPF at a significantly higher elongation than the elongation obtained when the nonwoven web made of mono-component spunbond fibers reaches its own PA-MPF.

Figure 13A:
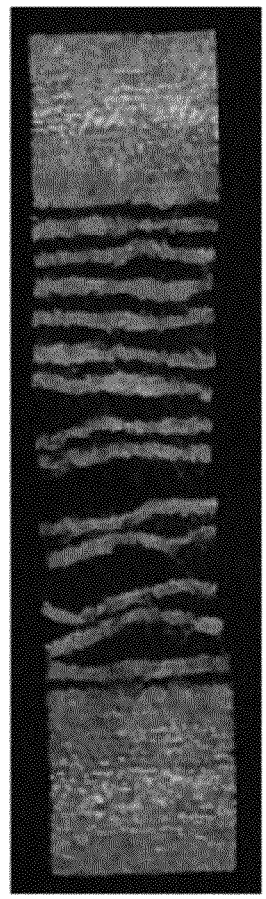
FIGS. 13A-13E are photographs of various webs after mechanical activation of a laminate that are delaminated from the laminate.
Figure 13B:
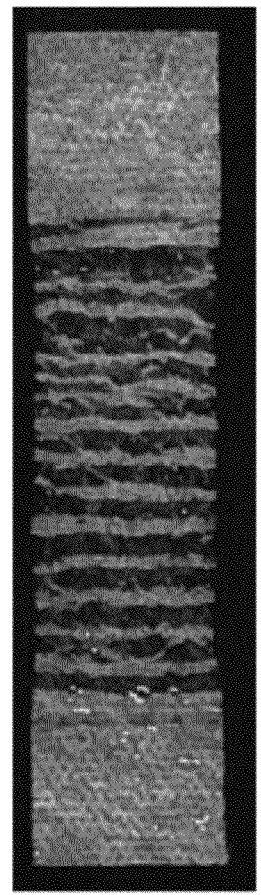
Figure 13C:
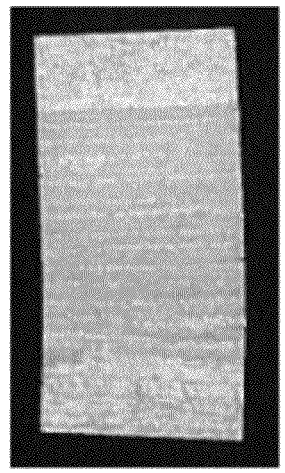
Figure 13D:
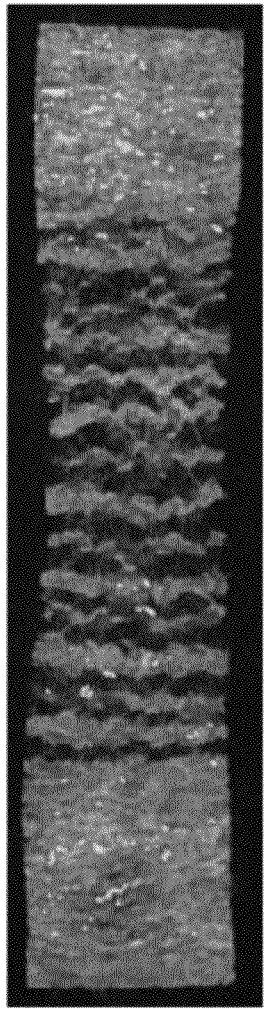
Figure 13E:
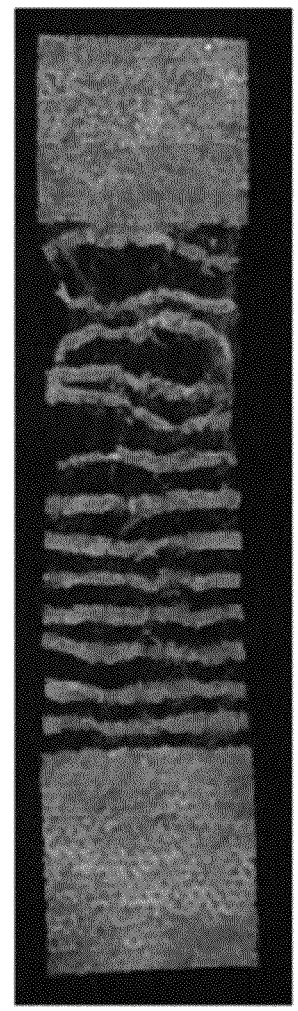
Figure 14:
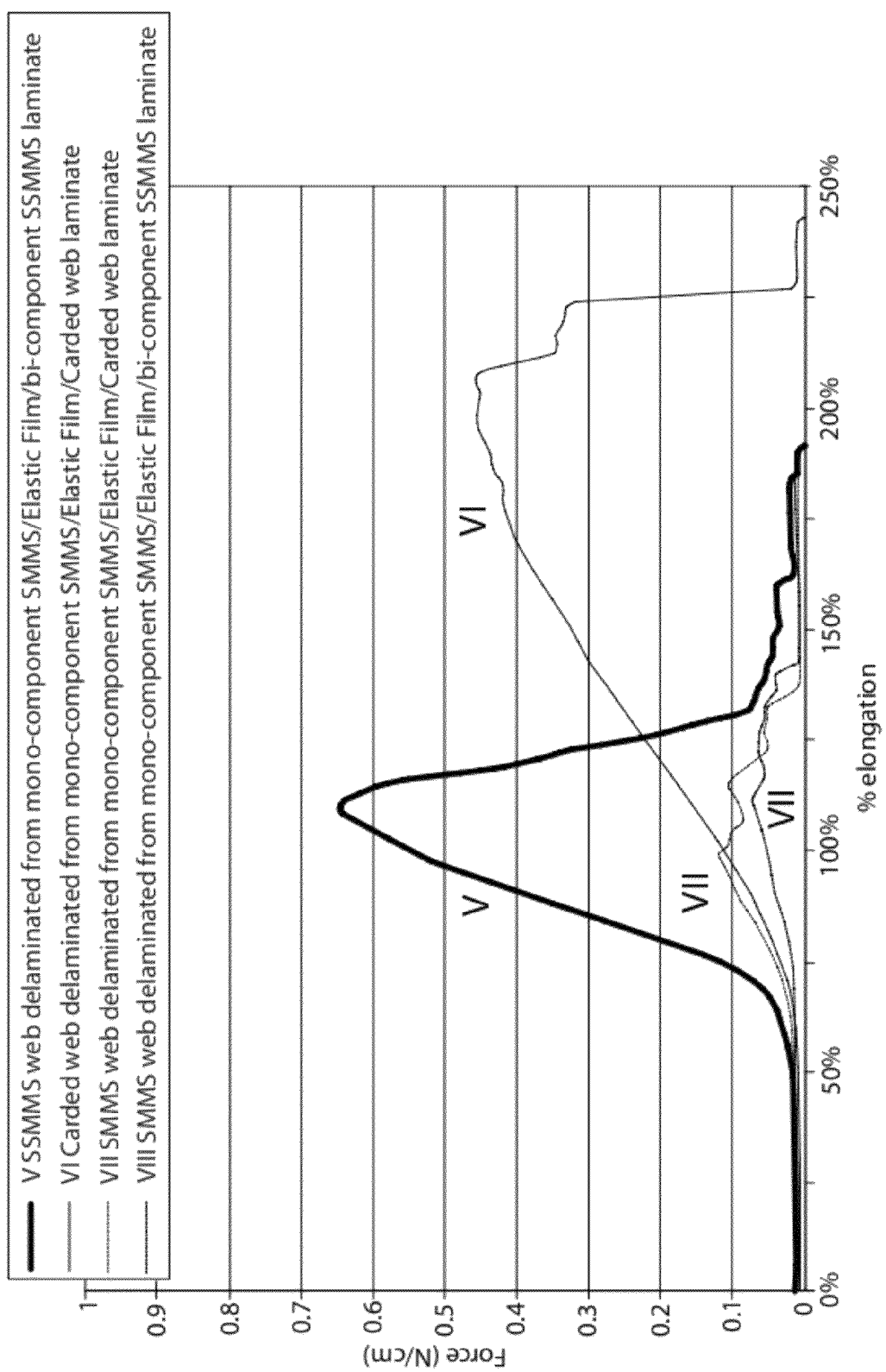
FIG. 14 represents tensile curves for various delaminated nonwoven webs after mechanical activation.

In order to confirm the benefit of a nonwoven web comprising the spunbond bi-component fibers previously described, two different examples of stretchable laminates are made and activated. A first stretchable laminate is made and comprises a first nonwoven web layer similar to the one previously discussed and identified by Roman numeral I that is bonded to one side of an elastic film and a second nonwoven web similar to the one previously discussed and identified by Roman numeral II is bonded to the other side of the elastic film. Both nonwoven webs are bonded to the film with a hotmelt adhesive. A second stretchable laminate is also made and comprises a first nonwoven web layer similar to the one previously discussed and identified by Roman numeral II that is bonded to one side of an elastic film and a second nonwoven web similar to the one previously discussed and identified by Roman numeral III is bonded to the other side of the elastic film. Both nonwoven webs are bonded to the film with a hotmelt adhesive. All of the layers used to make the first and second examples of stretchable laminates have a Machine Direction equal or greater than 25 mm and a Cross Machine Direction equal or greater than 75 mm. A central portion that includes the film layer and measuring approximately 40 mm of each of the stretchable laminates is mechanically activated by passing this 40 mm central portion between a pair of pressure applicators having three-dimensional surfaces which at least to a degree are complementary to one another at a Depth of Engagement of approximately 6 mm. A more detailed description of a suitable mechanical activation process is provided below. It should be noted that these two stretchable laminates are subjected to the same amount or level of mechanical activation. A laminate specimen measuring 75 mm (along the CD of the laminate) by 25 mm (along the MD of the laminate) of each of the laminate examples is cut such that the 40 mm central region that has previously been activated is centered on each laminate specimen. The nonwoven webs on each side of the stretchable laminate specimen are then removed from the elastic film by first soaking the specimen into acetone for about 15 seconds in order to dissolve the adhesive and then delicately remove the nonwoven web from the elastic film. In the event the adhesive does not dissolve any other solvent that can dissolve the adhesive without significantly damaging the nonwoven web can be used. Once the delaminated nonwoven web is removed from the film, the specimen should be left to dry for approximately 30 minutes before further testing. FIGS. 13A-13B are pictures (taken on a dark background for clarity) showing one example of the elastic film and each of the nonwoven webs after the webs are removed from the film. It can be observed in the pictures shown in FIGS. 13A and 13E that the nonwoven webs that include layers of mono-component spunbond fibers are visibly torn in the areas of the web that have been subjected to mechanical activation. In contrast, it can be observed that although the nonwoven web made of carded staple fibers (FIG. 13D) and the nonwoven web that includes layers of bi-component spunbond fibers (FIG. 13B) are highly elongated, the areas that are subjected to mechanical activation are not torn and many fibers are present in the portions that are mechanically activated. FIG. 13 is a picture of a typical film after removal of the nonwoven webs. The tensile curve of these mechanically activated nonwoven webs (removed from the elastic film) is measured in order to determine whether these mechanically activated nonwoven webs may still oppose further elongation. The tensile curve of each nonwoven web specimen is obtained under a different tensile test that is intended to mimic actual use of the laminate. This second test is done following EDANA method 20.2-89 with the following changes. Each specimen measures 75 mm (along the CD of the web) by 25 mm (along the MD of the web) and the tensile curve of the specimen is obtained by gripping the edges parallel to the Machine Direction of the specimen with clamps connected to a tensile tester such as a tester from MTS. The gauge length (i.e. clamp to clamp separation) is approximately 70 mm. The tensile curve is obtained at a cross-head displacement speed of approximately 2 mm/s. The elongation of each specimen is reported on the x axis in percent elongation while the force applied to each sample is reported on the y axis in Newton per centimeter (N/cm). The specimen is pulled until it ruptures (i.e. the post peak force response reaches a value less than 10% of the peak force). The tensile curve of each of these mechanically activated nonwoven webs is represented in FIG. 14. The tensile curve indicated by Roman numeral V is obtained for a SSMMS web that includes bi-component fibers and is delaminated from a mono-component SMMS/elastic film/SSMMS laminate. The tensile curve indicated by Roman numeral VI is obtained for a web of carded staple fibers and is delaminated from a mono-component SMMS/elastic film/Carded web laminate. The tensile curve indicated by Roman numeral VII is obtained for a SMMS web that is made of mono-component fibers and is delaminated from a mono-component SMMS/elastic film/Carded web laminate. The tensile curve indicated by Roman numeral VIII is obtained for a SMMS web that is made of mono-component fibers and is delaminated from a mono-component SMMS/elastic film/SSMMS laminate. One possible way to characterize such nonwoven webs after removal from the stretchable laminate is to determine their Residual Maximum Peak Force (hereinafter "R-MPF"). By "Residual Maximum Peak Force" it is meant the maximum peak force of at least one of the nonwoven webs used to form a stretchable laminate after at least a portion of the stretchable laminate is activated. It can be observed that the nonwoven webs that include layers of mono-component spunbond fibers oppose very little resistance to elongation. The R-MPF of the mono-component SMS web indicated by Roman numeral VII is less than approximately 0.15 N/cm and the R-MPF of the mono-component SMS web indicated by Roman numeral VIII is less than approximately 0.1 N/cm. The R-MPF of the nonwoven web that includes bi-component fibers and is indicated by Roman numeral V is at least approximately 0.6 N/cm while the R-MPF of the mono-component carded web indicated by Roman numeral VI is at least approximately 0.45 N/cm. It is believed that these results confirm that these nonwoven webs have been significantly torn or shredded during mechanical activation of the stretchable laminate. In contrast, the nonwoven webs made of carded staple fibers and the nonwoven web that includes layers of bi-component spunbond fibers are still able to resist elongation and contribute to the strength of the stretchable laminate. It can be advantageous for any of the previously described stretchable laminate to include a nonwoven web comprising bi-component spunbond fibers such that this nonwoven spunbond web has a R-MPF of at least 0.3 N/cm, at least 0.4 N/cm or even at least 0.5 N/cm. It may also be advantageous for any of the previously described stretchable laminate to include a nonwoven web comprising bi-component spunbond fibers such that this nonwoven spunbond web has a R-MPF of less than 2.5 N/cm, less than 2 N/cm, less than 1.5 N/cm or even less than 1 N/cm. It is believed that a nonwoven web that has bi-component spunbond fibers (preferably of the core/sheath type) is capable of enduring mechanical activation at a higher depth of engagement and/or a higher speed than a nonwoven web that is made exclusively of mono-component fibers. As a result, a stretchable laminate including such a nonwoven web and an elastic film having a given basis weight and tensile properties may also be activated to a higher level. In the alternative, a stretchable laminate including such a nonwoven web with bi-component fibers and an elastic film having a reduced basis weight and/or tensile properties may be activated to substantially the same level as a stretchable laminate having a nonwoven web made of mono-component fibers and an elastic film having a greater basis weight and/or tensile properties.

Figure 15:
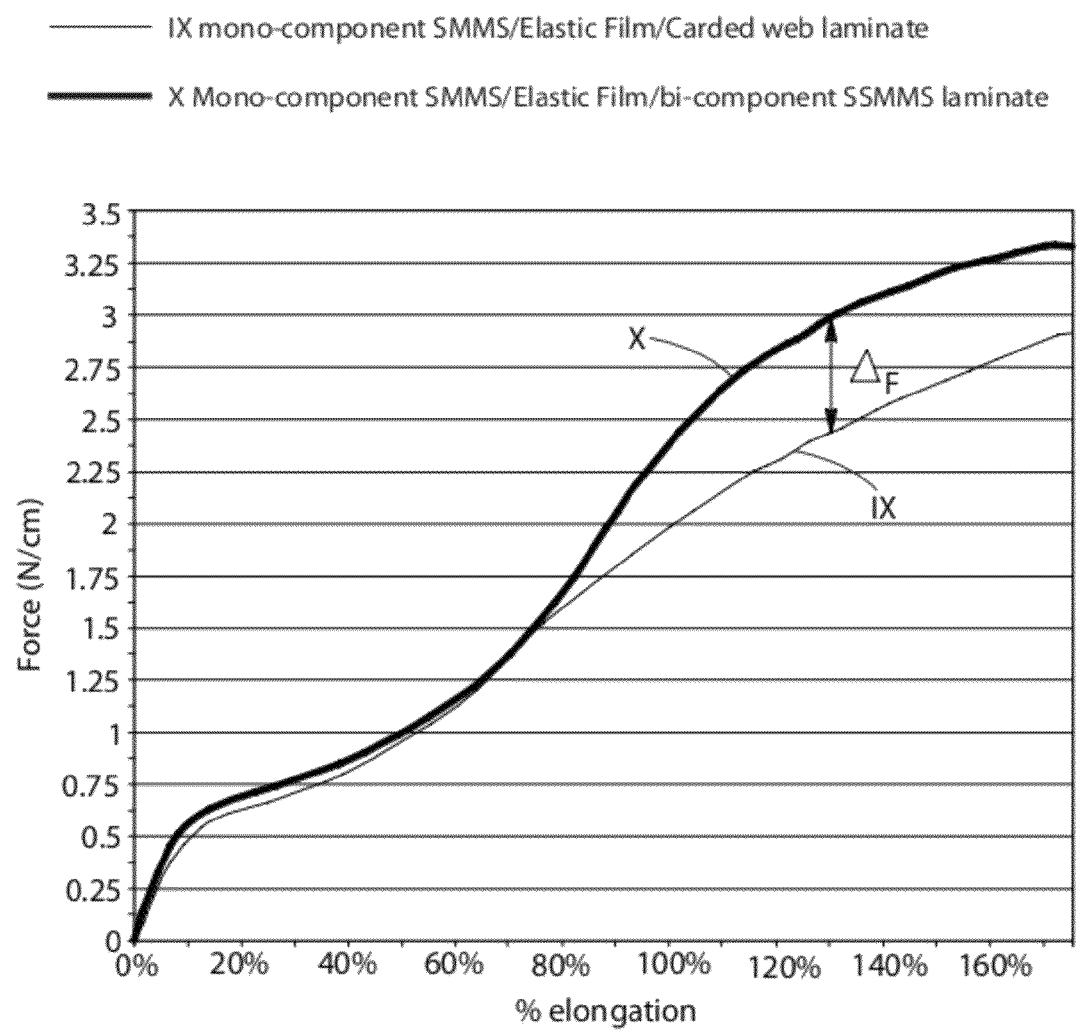
FIG. 15 represents tensile curves of two stretchable laminates after mechanical activation.

As further discussed below, any of the previously described stretchable laminates may be used as components of disposable absorbent articles (for example diapers or pants) that may include stretchable ears or side panels. Disposable absorbent articles that are commercially available include stretchable ears or side panels which are made from a stretchable laminate comprising nonwoven webs made of mono-component fibers. It is typical for a caregiver or a user to elongate the ears or side panel from 85% to 125% of the ear or side panel original length. It is believed that an elongation from 85% to 125% of the stretchable element original length, provides adequate fit and comfort to the wearer. However, it is also believed that some caregivers and users may (knowingly or unknowingly) elongate these stretchable elements well above 125% of the element's original length. Such a high elongation may result in the wearer feeling some discomfort but it may also result in the tearing of stretchable element which, in turn, renders the absorbent article unusable. It is believed that these drawbacks may be minimized in not eliminated by providing a stretchable element made of any of the previously described stretchable laminates (that include a nonwoven web with bi-component fibers) that can signal to the caregiver or the user that the stretchable element should not be elongated any further. This signal may be provided by way of a stretchable laminate whose resistance to elongation increases noticeably when the stretchable element is elongated more than 100% of its original relaxed length. FIG. 15 represents the tensile curves that are obtained for two different stretchable laminates. The first stretchable laminate (indicated by Roman numeral IX) includes a nonwoven SMMS web made of mono-component fibers (having an aggregate basis weight of 17 g/m$^2$), an elastic film (having a basis weight of 54.5 GSM) which is a coextruded film having styrene block copolymer elastomeric core and polyolefin skin, and a web of carded mono-component fibers (having a basis weight of 27 g/m$^2$).

The second stretchable laminate (indicated by Roman numeral X) includes a nonwoven SMMS web made of monocomponent fibers (having an aggregate basis weight of 17 g/m$^2$), an elastic film (having a basis weight of 54.5 g/m$^2$) similar to the one previously discussed and a SSMMS web that includes bi-component spunbond fibers (having an aggregate basis weight of 20 g/m$^2$). It can be observed that these tensile curves are substantially identical up to an elongation of 80% of the laminate's original length. It can also be observed that the force required to elongate the stretchable laminate that has a SSMMS web that includes bi-component spunbond fibers is greater than the force required to elongate the stretchable laminate that has a web of carded monocomponent fibers when the stretchable laminates are elongated more than 85% of their respective original length. The difference between the amount of force required to elongate both laminates (herein after "$\Delta_F$") can be as high as approximately 0.5N/cm at an elongation from 110% to 160% of the stretchable laminates original length. It is believed that a caregiver or a user may start noticing this increased resistance to elongation when he or she attempts to elongate the stretchable element (including several cm$^2$ of the stretchable laminate) of an article beyond 85% of the stretchable element original length. It is also believed that an increased resistance to elongation may communicate to the caregiver or user that the stretchable element should not be elongated any further. It is further believed that the residual resistance to elongation of a web (in particular in a web including bi-component fibers) after the laminate is mechanically activated, provides the increased resistance to elongation that occurs when the stretchable laminate is elongated more than 85% of its original length. It can be advantageous for any of the previously described stretchable laminate to include a nonwoven web that comprises bi-component spunbond fibers and that is such that the force required to elongate this web after mechanical activation of stretchable laminate at an elongation of between 85% and 125% is between 0.2 N/cm and 1.5 N/cm, between 0.3 N/cm and 1.2 N/cm or even between 0.4 N/cm and 1 N/cm. It is believed that a nonwoven web that has bi-component spunbond fibers (preferably of the core/sheath type) can conveniently be used to make a stretchable laminate that will provide a noticeable resistance to elongation when a stretchable element made of this stretchable material is elongated more than 85% of its original length.

Figure 16:
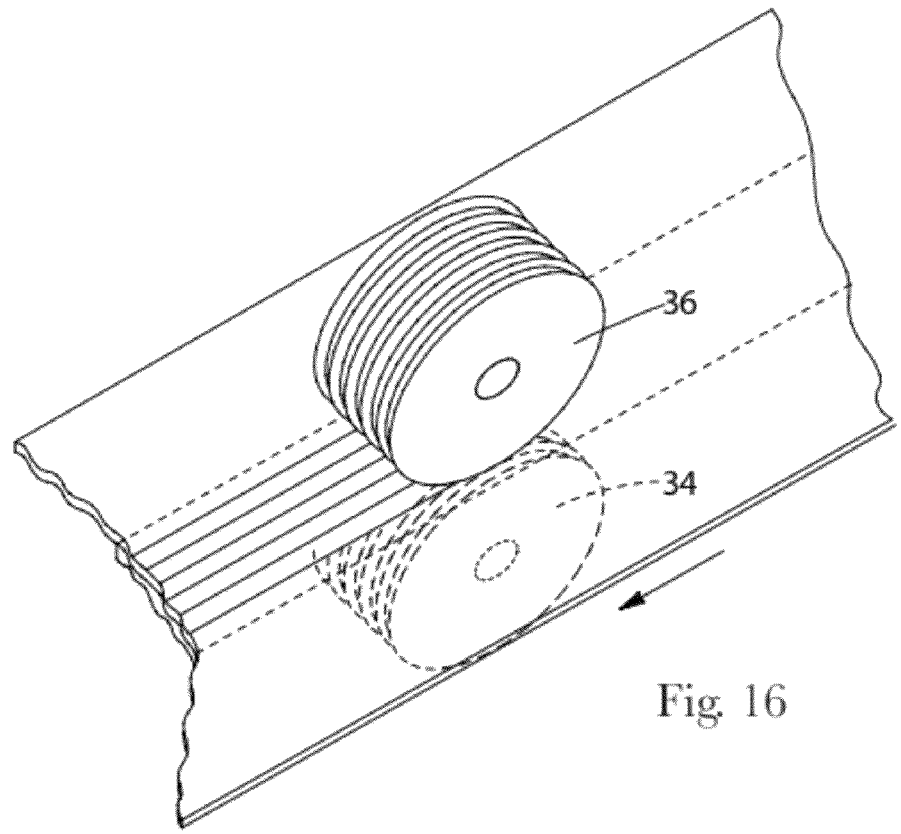
FIG. 16 is a schematic representation of a device for mechanically activating a stretchable laminate.
Figure 17:
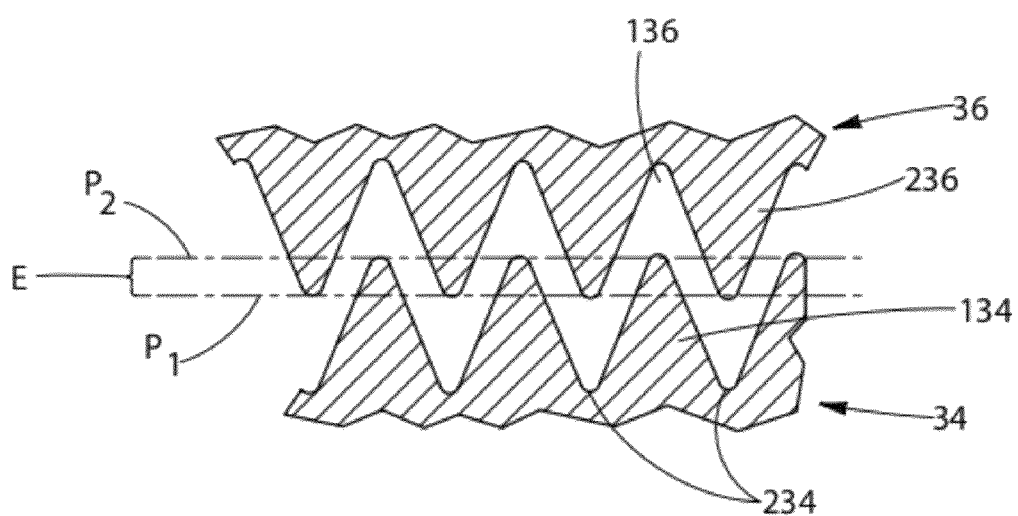
FIG. 17 is a schematic cross-sectional view of a device for mechanically activating a stretchable laminate.

Mechanical Activation of a Laminate:

Any of the previously discussed stretchable laminate can be mechanically activated (i.e. pre-strained) such that the laminate recovers some of the elasticity it lost when all the webs forming the laminate are bonded together. A non-limiting example of a process for mechanically activating a stretchable laminate is schematically represented in FIGS. 16 and 17. The device shown in those figures include a pair of pressure applicators 34, 36 having three-dimensional surfaces which at least to a degree are complementary to one another. A pressure applicator (or roler) includes at least one engaging portion or tooth 134 (but may also include a plurality) corresponding to a recess portion 136 of the other pressure applicator. A pressure applicator preferably includes a plurality of engaging portions or teeth 134 and recess portions 234 that can intermesh with a corresponding recess portions 136 and engaging portions or teeth 236 on the other pressure applicator. When the laminate passes in between the pressure applicators 34, 36, portions of the laminate are strained. The stretchable laminate is able to relax and return substantially to its original width as it "exits" the pressure applicators. The degree of mechanical activation may be adjusted by varying the number of engaging portions and recess portions and the depth of engagement of the pressure applicators on the stretchable laminate. One of ordinary skill in the art will appreciate that other processes for mechanically activating a stretchable laminate may be used and still provide the same benefits.

With reference to FIG. 17, which shows a portion of the intermeshing of the engaging portions 134 and 236 of pressure applicators 34 and 36, respectively, the term "pitch" refers to the distance between the apexes of adjacent engaging portions. The pitch can be between approximately 0.02 to approximately 0.30 inches (0.51-7.62 mm), and is preferably between approximately 0.05 and approximately 0.15 inches (1.27-3.81 mm). The height (or depth) of the teeth is measured from the base of the tooth to the apex of the tooth, and is preferably equal for all teeth. The height of the teeth can be between approximately 0.10 inches (2.54 mm) and 0.90 inches (22.9 mm), and is preferably approximately 0.25 inches (6.35 mm) and 0.50 inches (12.7 mm). The engaging portions 134 in one pressure applicator can be offset by one-half the pitch from the engaging portions 236 in the other pressure applicator, such that the engaging portions of one pressure applicator (e.g., engaging portion 134) mesh in the recess portions 136 (or valleys) located between engaging portions in the corresponding pressure applicator. The offset permits intermeshing of the two pressure applicators when the pressure applicators are "engaged" or in an intermeshing, operative position relative to one another. In one embodiment, the engaging portions of the respective pressure applicators are only partially intermeshing. The degree to which the engaging portions on the opposing pressure applicators intermesh is referred to herein as the "depth of engagement" or "DOE" of the engaging portions. As shown in FIG. 17, the DOE is the distance between a position designated by plane P1 where the apexes of the engaging portions on the respective pressure applicators are in the same plane (0% engagement) to a position designated by plane P2 where the apexes of the engaging portions of one pressure applicators extend inward beyond the plane P1 toward the recess portions on the opposing pressure applicator. The optimum or effective DOE for particular laminates is dependent upon the height and the pitch of the engaging portions and the materials of the web. In other embodiments the teeth of the mating rolls need not be aligned with the valleys of the opposing rolls. That is, the teeth may be out of phase with the valleys to some degree, ranging from slightly offset to greatly offset.

Figure 18:
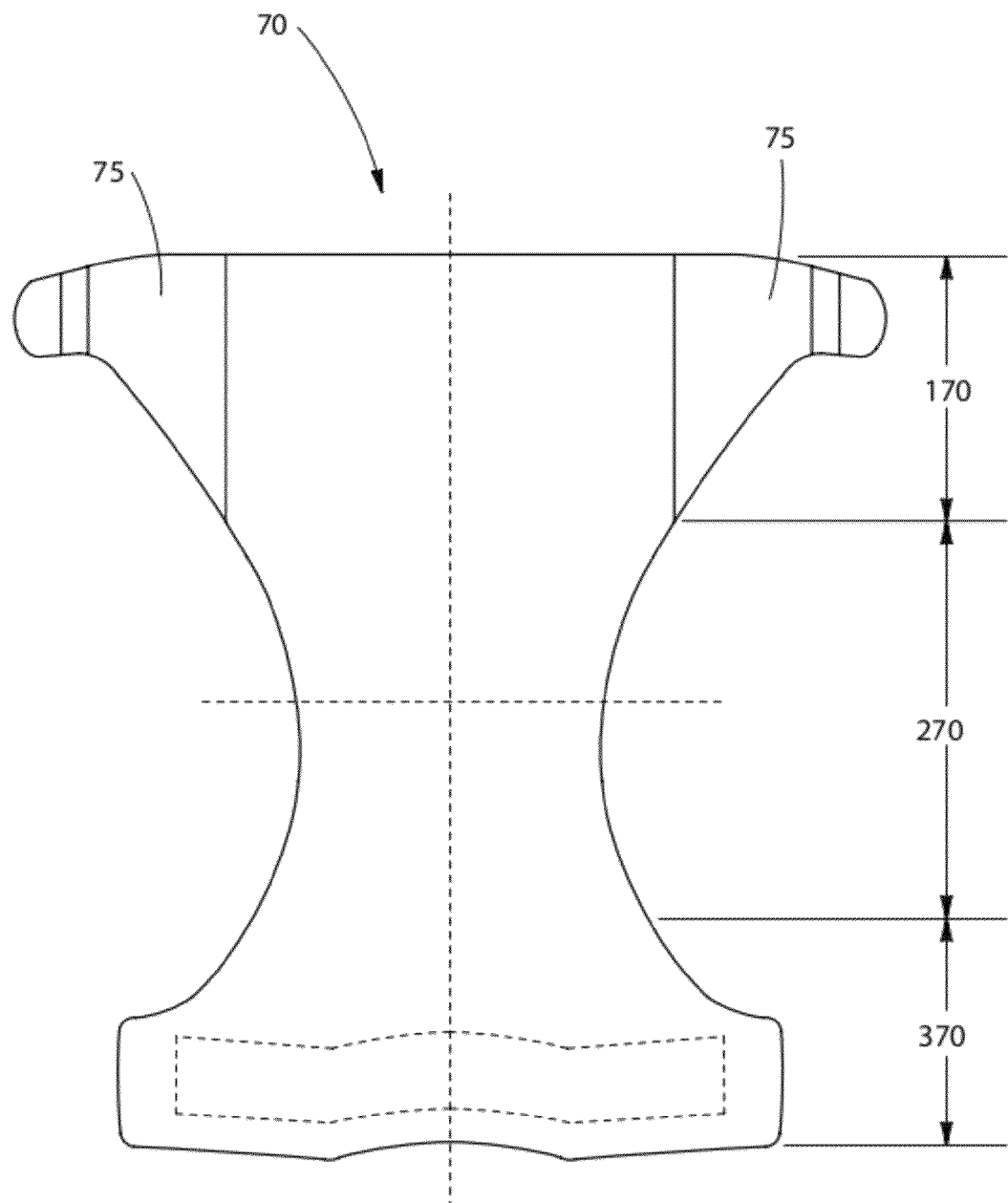
FIG. 18 is a schematic representation of a disposable absorbent article.
Figure 19:
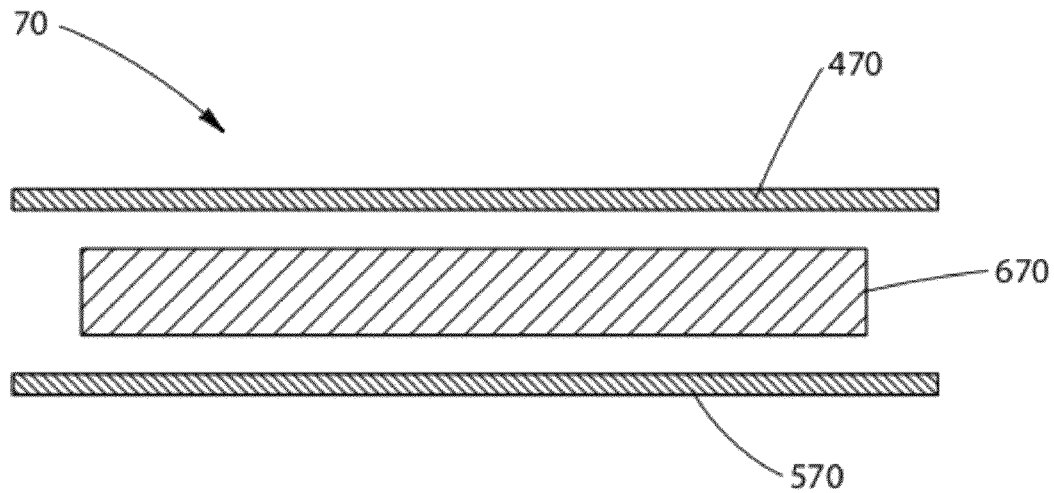
FIG. 19 is a schematic cross-sectional representation of a disposable absorbent article.

A laminate including any of the webs previously discussed may be adapted for use in a disposable absorbent article such as a diaper, a pant, an adult incontinence product a sanitary napkin or any other article that may benefit from having at least a portion thereon that is elastically stretchable. In one embodiment, ears or side panels may be cut from such a stretchable laminate and one side edge of the ear may be attached to the chassis of a disposable absorbent article. A disposable absorbent article 70 that include a back waist region 170, a crotch region 270 and a front waist region 370 is schematically represented in FIG. 18. A pair of ears 75 are attached along their respective proximal edge to the left and right sides of the disposable absorbent article respectively. A fastener such as a mechanical comprising a plurality of extending hooks or an adhesive may be connected to a portion of the ear or side panel about the distal edge of the ear or side panel. Such a fastener may in combination with the laminate stretchability provide for proper placement and attachment of the absorbent article about the lower torso of a wearer. In another embodiment, any such laminate may be used as an integral outer cover for an absorbent article. A typical chassis of a disposable absorbent article 70 may include a liquid pervious top sheet 470, a liquid impervious backsheet 570 and an absorbent core 670 disposed between the topsheet and the backsheet and are schematically represented in FIG. 19. An absorbent article may also include any features that may be suitable for such an article and are known in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stretchable laminate comprising:
   a. a first nonwoven web, said first nonwoven web comprising:
      a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and a cross-machine direction;
      a second layer of fibers comprising meltblown fibers, said second layer having a top and a bottom surface wherein said top surface of said second layer faces said bottom surface of said first layer; and
      a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;
      wherein said first nonwoven web comprises a plurality of thermo-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction;
      and
   b. a web of an elastomeric material having top and bottom surfaces,
      wherein the bottom surface of said third layer comprising spunbond fibers of said first nonwoven web is bonded to said top surface of said elastomeric web to form a laminate.

2. The stretchable laminate of claim 1 wherein the melt temperature of said second polymer forming said sheath is less than about 150°.

3. The stretchable laminate of claim 1 further comprising:
   c. a second nonwoven web bonded to the bottom surface of said elastomeric web comprising:
      a first layer comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a inner and an outer surface;
      a second layer of fibers comprising meltblown fibers said second layer having a top and a bottom surface wherein the bottom surface of said second layer faces the top surface of said first layer; and
      a third layer of fibers comprising spunbond fibers, said third layer having a top and a bottom surface wherein said spunbond fibers are multi-component fibers having a core comprising a first polymer having a first melt temperature and a sheath comprising a second polymer having a second melt temperature wherein said second melt temperature is lower than said first melt temperature, wherein the bottom surface of said third layer faces said top surface of said second layer such that said second layer is positioned between said first and third layers of said second nonwoven web;
      wherein said second nonwoven web comprises a plurality of thermo-bonds extending at least partially through said second nonwoven web, wherein the first polymer forming the core of said multi-component fibers has not melted within said thermo-bonds and the second polymer forming the sheath of said multi-component fibers has melted within said thermo-bonds,
      wherein the top surface of said third layer comprising spunbond fibers of said second nonwoven web is bonded to said bottom surface of said elastomeric web.

4. The stretchable laminate of claim 1 wherein said elastomeric web is a film comprising an elastomeric polyolefin.

5. The stretchable laminate of claim 1 wherein said first nonwoven web is adhesively bonded to said elastomeric web with a hotmelt adhesive having a melt temperature.

6. The stretchable laminate of claim 5 wherein the melt temperature of said hotmelt adhesive is greater than the melt temperature of said second polymer.

7. The stretchable laminate of claim 6 wherein the melt temperature of said hotmelt adhesive is lower than the melt temperature of said first polymer.

8. The stretchable material of claim 1 wherein at least a portion of said laminate is mechanically activated.

9. A process of making a stretchable laminate comprising:
   obtaining a first nonwoven web, said first nonwoven web comprising:

a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and za cross-machine direction;

a second layer of fibers comprising meltblown fibers, said second layer having a top and a bottom surface wherein said the top surface of said second layer faces said bottom surface of said first layer; and a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;

wherein said first nonwoven web comprises a plurality of thereto-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction;

obtaining a web of an elastomeric material having top and bottom surfaces; and bonding the bottom surface of one of said third layer comprising spunbond fibers of said first nonwoven web to said top surface of said elastomeric web.

10. The process of claim 9 wherein the melt temperature of said second polymer forming said sheath is less than about 150°.

11. The process of claim 9 further comprising:
bonding a second nonwoven web to the bottom surface of said elastomeric web.

12. The process of claim 11 wherein said second nonwoven web comprises:

a first layer comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a inner and an outer surface;

a second layer of fibers comprising meltblown fibers said second layer having a top and a bottom surface wherein the bottom surface of said second layer faces the top surface of said first layer; and a third layer of fibers comprising spunbond fibers, said third layer having a top and a bottom surface wherein said spunbond fibers are multi-component fibers having a core comprising a first polymer having a first melt temperature and a sheath comprising a second polymer having a second melt temperature wherein said second melt temperature is lower than said first melt temperature, wherein the bottom surface of said third layer faces said top surface of said second layer such that said second layer is positioned between said first and third layers of said second nonwoven web;

wherein said second nonwoven web comprises a plurality of thermo-bonds extending at least partially through said second nonwoven web, wherein the first polymer forming the core of said multi-component fibers has not melted within said thermo-bonds and the second polymer forming the sheath of said multi-component fibers has melted within said thermo-bonds, wherein the top surface of one of third layer comprising spunbond fibers of said second nonwoven web is bonded to said bottom surface of said elastomeric web.

13. The process of claim 9 wherein said elastomeric web is a film of an elastomeric material comprising an elastomeric polyolefin.

14. The process of claim 9 wherein said first nonwoven web is adhesively bonded to said elastomeric web with a hotmelt adhesive having a melt temperature that is greater than the melt temperature of said second polymer.

15. The process of claim 9 wherein said first nonwoven web is adhesively bonded to said elastomeric web with a hotmelt adhesive having a melt temperature that is greater than the melt temperature of said second polymer.

16. A disposable absorbent article comprising:

a chassis having opposing first and second longitudinal side edges, said chassis comprising a liquid pervious topsheet, a liquid impervious backsheet and an absorbent core disposed between said topsheet and said backsheet; and a pair of stretchable ears or side panels connected to each longitudinal side edge of said chassis, each of said ears or side panels comprising a stretchable laminate comprising:

a. a first nonwoven web, said first nonwoven web comprising:

a first layer of fibers comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a top and a bottom surface, a machine direction and a cross-machine direction;

a second layer of fibers comprising meltblown fibers, said second layer having a top and a bottom surface wherein said the top surface of said second layer faces said bottom surface of said first layer; and a third layer of fibers comprising spunbond fibers layer, said third layer having a top and a bottom surface, a machine direction and a cross-machine direction, wherein said spunbond fibers are multi-component fibers having a core comprising a first polymer having a first melt temperature and a sheath comprising a second polymer having a second melt temperature wherein said second melt temperature is lower than said first melt temperature, wherein the top surface of said third layer faces said bottom surface of said second layer such that said second layer is positioned between said first and third layers;

wherein said first nonwoven web comprises a plurality of thermo-bonds extending at least partially through said first nonwoven web, wherein the first polymer forming the core of said multi-component fibers has not melted within said thermo-bonds and the second polymer forming the sheath of said multi-component fibers has melted within said thermo-bonds such that at least some of said thermo-bonds are elongatable in said cross-machine direction; and;

b. a web of an elastomeric material having top and bottom surfaces, wherein the bottom surface of said third layer comprising spunbond fibers of said first nonwoven web is bonded to said top surface of said elastomeric web to form a laminate.

17. The absorbent article of claim 16 wherein the melt temperature of said second polymer forming said sheath is less than about 150°.

18. The absorbent article of claim 16 further comprising:

c. a second nonwoven web bonded to the bottom surface of said elastomeric web wherein said second nonwoven web comprises:
  a first layer comprising spunbond fibers wherein said spunbond fibers are multi-component fibers having a core comprising a first polymer having a first melt temperature and a sheath comprising a second polymer having a second melt temperature wherein said second melt temperature is lower than said first melt temperature, said first layer having a inner and an outer surface;
  a second layer of fibers comprising meltblown fibers said second layer having a top and a bottom surface wherein the bottom surface of said second layer faces the top surface of said first layer; and
  a third layer of fibers comprising spunbond fibers, said third layer having a top and a bottom surface wherein said spunbond fibers are multi-component fibers having a core comprising a first polymer having a first melt temperature and a sheath comprising a second polymer having a second melt temperature wherein said second melt temperature is lower than said first melt temperature, wherein the bottom surface of said third layer faces said top surface of said second layer such that said second layer is positioned between said first and third layers of said second nonwoven web;
  wherein said second nonwoven web comprises a plurality of thermo-bonds extending at least partially through said second nonwoven web, wherein the first polymer forming the core of said multi-component fibers has not melted within said thermo-bonds and the second polymer forming the sheath of said multi-component fibers has melted within said thermo-bonds,
  wherein the top surface of said third layer comprising spunbond fibers of said second nonwoven web is bonded to said bottom surface of said elastomeric web.

19. The disposable absorbent article of claim 16 wherein said elastomeric web is a film comprising an elastomeric polyolefin.

20. The disposable absorbent article of claim 16 wherein at least a portion of said stretchable laminate is mechanically activated.

* * * * *

UNITED STATES PATENT AND TRADEMARK OFFICE
CERTIFICATE OF CORRECTION

PATENT NO.         : 8,231,595 B2
APPLICATION NO.    : 12/756226
DATED              : July 31, 2012
INVENTOR(S)        : Robert Haines Turner et al.

It is certified that error appears in the above-identified patent and that said Letters Patent is hereby corrected as shown below:

<u>Column 25</u>
Line 27, delete "thereto" and insert --thermo--.

Signed and Sealed this
Second Day of October, 2012

David J. Kappos
*Director of the United States Patent and Trademark Office*